(12) United States Patent
Englebienne

(10) Patent No.: US 7,521,435 B2
(45) Date of Patent: Apr. 21, 2009

(54) SILICON CONTAINING COMPOUNDS HAVING SELECTIVE COX-2 INHIBITORY ACTIVITY AND METHODS OF MAKING AND USING THE SAME

(75) Inventor: Patrick Englebienne, Zingem (BE)

(73) Assignee: Pharma Diagnostics, N.V., Zingem (BE)

( * ) Notice: Subject to any disclaimer, the term of this patent is extended or adjusted under 35 U.S.C. 154(b) by 5 days.

(21) Appl. No.: 11/356,715

(22) Filed: Feb. 16, 2006

(65) Prior Publication Data

US 2006/0258619 A1 Nov. 16, 2006

Related U.S. Application Data

(60) Provisional application No. 60/654,174, filed on Feb. 18, 2005.

(51) Int. Cl.
*A01N 31/70* (2006.01)
*A61K 31/695* (2006.01)

(52) U.S. Cl. ............... 514/63; 546/14; 548/110; 556/413

(58) Field of Classification Search ............ 514/473, 514/471, 406, 63; 549/319, 313; 546/14; 548/110; 556/413
See application file for complete search history.

(56) References Cited

U.S. PATENT DOCUMENTS

| | | | |
|---|---|---|---|
| 5,474,995 A | 12/1995 | Ducharme et al. | |
| 5,536,752 A | 7/1996 | Ducharme et al. | |
| 5,550,142 A | 8/1996 | Ducharme et al. | |
| 5,633,272 A | 5/1997 | Talley et al. | |
| 5,710,140 A | 1/1998 | Ducharme et al. | |
| 5,719,163 A | 2/1998 | Norman et al. | |
| 5,859,257 A | 1/1999 | Talley | |
| 5,945,539 A | 8/1999 | Haruta et al. | |
| 5,985,902 A | 11/1999 | Talley et al. | |
| 5,994,381 A | 11/1999 | Haruta et al. | |
| 6,002,014 A | 12/1999 | Haruta et al. | |
| 6,040,341 A | 3/2000 | Del Soldato et al. | |
| 6,071,954 A * | 6/2000 | LeBlanc et al. | 514/473 |
| 6,297,260 B1 | 10/2001 | Bandarage et al. | |
| 6,362,209 B1 | 3/2002 | Haruta et al. | |
| 6,416,861 B1 * | 7/2002 | Lee et al. | 428/391 |
| 6,436,967 B1 | 8/2002 | Talley et al. | |
| 6,482,956 B2 | 11/2002 | Luengo et al. | |
| 6,673,818 B2 | 1/2004 | Brown et al. | |
| 6,699,884 B2 | 3/2004 | Brown et al. | |
| 7,087,630 B2 | 8/2006 | Bandarage et al. | |
| 2003/0161875 A1 * | 8/2003 | Murpani et al. | 424/465 |
| 2004/0006133 A1 | 1/2004 | Ranatunge et al. | |
| 2004/0072883 A1 | 4/2004 | Garvey et al. | |
| 2004/0082652 A1 | 4/2004 | Del Soldato et al. | |
| 2005/0032851 A1 | 2/2005 | Talley et al. | |
| 2005/0032852 A1 | 2/2005 | Carter | |
| 2005/0101661 A1 | 5/2005 | Soldato et al. | |

FOREIGN PATENT DOCUMENTS

| | | | |
|---|---|---|---|
| JP | 61197607 | * | 9/1986 |
| WO | WO 95/18799 | | 7/1995 |
| WO | WO 96/25405 | | 8/1996 |
| WO | WO 96/36617 | | 11/1996 |
| WO | WO 97/38986 | | 10/1997 |
| WO | WO 95/15316 | | 6/1998 |
| WO | WO 00/25776 | | 5/2000 |
| WO | WO 01/45703 | | 6/2001 |
| WO | WO 2004/000300 | | 12/2003 |
| WO | WO 2004/000781 | | 12/2003 |
| WO | WO 2004/024186 | | 3/2004 |
| WO | WO 2005/030224 | | 4/2005 |
| WO | WO 2005/044825 | * | 5/2005 |

\* cited by examiner

*Primary Examiner*—Daniel M Sullivan
*Assistant Examiner*—Chukwuma O Nwaonicha
(74) *Attorney, Agent, or Firm*—Bozicevic, Field & Francis, LLP; Bret E. Field

(57) ABSTRACT

Silicon-containing compounds having selective COX-2 inhibitory activity, as well as compositions thereof are provided. The subject compounds find use in a variety of applications, including therapeutic applications. Also provided are kits containing the subject compounds and pharmaceutical preparations thereof.

4 Claims, 13 Drawing Sheets

SC-558 (1)

Celecoxib (2)

Figure 1:
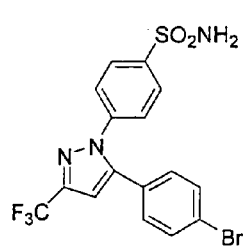
Figure 1:
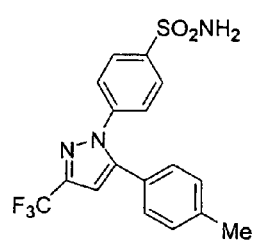
Figure 1:
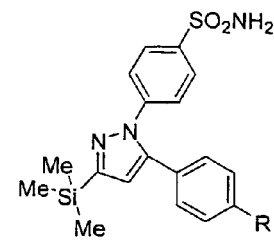
Figure 1:
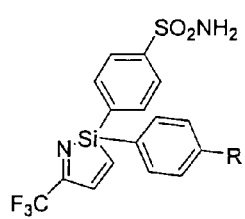
Figure 1:
Figure 1:
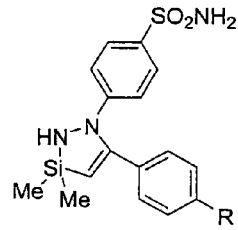
Figure 1:
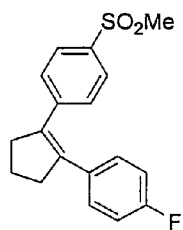
Figure 1:
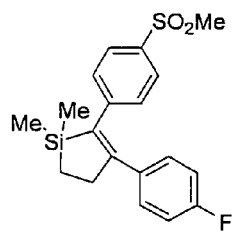
Figure 1:
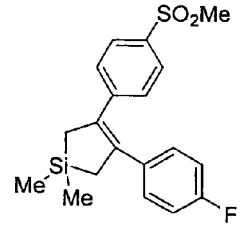
Figure 1:
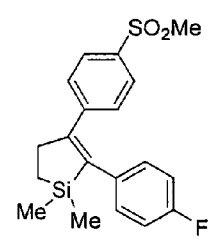
Figure 1:
Figure 1:
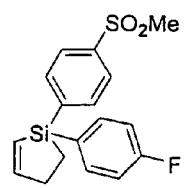

1a R= Br
2a R= Me

1b R= Br
2b R= Me

1c R= Br
2c R= Me

1d R= Br
2d R= Me

SC-57666 (3)

3a

3b

3c

3d

3e

FIGURE 8A

Table 1. Identification and physico-chemical characteristics of the model and sila-substituted compounds evaluated.

| # | Common Name | IUPAC name | M.W. | Molecular Volume ($Å^3$) | Molecular Surface ($Å^2$) | Calculated Log P |
|---|---|---|---|---|---|---|
| 1 | Sc-558 | 4-[5-(4-Bromophenyl)-3-trifluoromethyl-pyrazol-1-yl]-benzenesulfonamide | 446.24 | 294.14 | 345.42 | 3.62 |
| 1a | | 4-[5-(4-Bromophenyl)-3-trimethylsilanyl-pyrazol-1-yl]-benzenesulfonamide | 450.43 | 338.07 | 400.64 | 3.94 |
| 1b | | 2-(4-Bromophenyl)-2-(4-methanesulfonylphenyl)-5-trifluoromethyl-2H-[1,2]azasilole | 461.33 | 299.88 | 351.88 | 3.87 |
| 1c | | 4-[3-(4-Bromophenyl)-5-trifluoromethyl-3H-[1,2,3]diazasilol-3-yl]-benzenesulfonamide | 462.32 | 296.3 | 351.37 | 3.86 |
| 1d | | 4-[5-(4-Bromophenyl)-3,3-dimethyl-2,3-dihydro-[1,2,3]diazasilol-1-yl]-benzenesulfonamide | 424.39 | 311.34 | 367.02 | 3.57 |
| 2 | Celecoxib | 4-(5-p-Tolyl-3-trifluoromethyl-pyrazol-1-yl)-bezenesulfonamide | 381.37 | 289.80 | 345.76 | 3.27 |
| 2a | | 4-(5-p-Tolyl-3-trimethylsilanyl-pyrazol-1-yl)-bezenesulfonamide | 385.56 | 333.58 | 398.97 | 3.56 |
| 2b | | 4-(2-p-Tolyl-5-trifluoromethyl-2H-[1,2]azasilol-2-yl)-bezenesulfonamide | 396.46 | 295.19 | 350.14 | 3.47 |
| 2c | | 4-(3-p-Tolyl-5-trifluoromethyl-3H-[1,2,3]diazasilol-3-yl)-bezenesulfonamide | 397.45 | 292.24 | 350.55 | 3.81 |
| 2d | | 4-(3,3-Dimethyl-5-p-tolyl-2,3-dihydro-[1,2,3]diazasilol-1-yl)-bezenesulfonamide | 359.52 | 306.9 | 367.52 | 3.14 |
| 3 | Sc-57666 | 1-(4-Methanesulfonylphenyl)-2-(4-fluorophenyl)-cyclopentene | 316.39 | 272.64 | 321.73 | 3.77 |
| 3a | | 4-(4-Fluorophenyl)-5-(4-methanesulfonylphenyl)-1,1-dimethyl-2,3-dihydro-1H-silole | 360.52 | 311.13 | 367.26 | 4.25 |
| 3b | | 3-(4-Fluorophenyl)-4-(4-methanesulfonylphenyl)-1,1- | 360.52 | 317.88 | 386.45 | 4.29 |

FIGURE 8A CONTINUED

| # | Common Name | IUPAC name | M.W. | Molecular Volume (Å³) | Molecular Surface (Å²) | Calculated Log P |
|---|---|---|---|---|---|---|
| | | dimethyl-2,5-dihydro-1H-silole | | | | |
| 3c | | 5-(4-Fluorophenyl)-4-(4-methanesulfonylphenyl)-1,1-dimethyl-2,3-dihydro-1H-silole | 360.52 | 312.76 | 371.21 | 4.26 |
| 3d | | 1-(4-Fluorophenyl)-1-(4-methanesulfonylphenyl)-silolane | 334.48 | 281.14 | 331.58 | 3.83 |
| 3e | | 1-(4-Fluorophenyl)-1-(4-methanesulfonylphenyl)-2,3-dihydro-1H-silole | 332.47 | 272.90 | 322.16 | 3.83 |
| 4 | Valdecoxib | 4-(5-Methyl-3-phenyl-isoxazol-4-yl)-benzenesulfonamide | 314.36 | 258.3 | 301.26 | 3.30 |
| 4a | | 4-(3-Phenyl-5-trimethylsilanyl-isoxazol-4-yl)-benzenesulfonamide | 372.52 | 313.36 | 364.36 | 3.78 |
| 4b | | 4-(5-Methyl-4-phenyl-4,5-dihydro-[1,2,4]oxazasilol-4-yl)-benzenesulfonamide | 332.45 | 265.86 | 307.12 | 2.36 |
| 4c | | 4-(5-Methyl-3-phenyl-2,3-dihydro-[1,2,3]oxazasilol-3-yl)-benzenesulfonamide | 332.45 | 263.26 | 312.57 | 2.94 |
| 4d | | 4-(5,5-Dimethyl-3-phenyl-4,5-dihydro-[1,2,5]oxazasilol-4-yl)-benzenesulfonamide | 346.48 | 293.06 | 349.78 | 3.43 |
| 5 | Rofecoxib | 4-(4-Methanesulfonylphenyl)-3-phenyl-5H-furan-2-one | 314.36 | 262.18 | 308.11 | 2.51 |
| 5a | | 3-(4-Methanesulfonylphenyl)-2,2-dimethyl-4-phenyl-2H-[1,2]oxasilol-5-one | 358.49 | 301.39 | 352.29 | 3.44 |
| 5b | | 3-(4-Methanesulfonylphenyl)-3-phenyl-[1,3]oxasilolan-5-one | 332.45 | 270.98 | 318.25 | 3.35 |
| 5c | | 3-(4-Methanesulfonylphenyl)-3-phenyl-3H-[1,3]oxasilol-2-one | 330.43 | 259.92 | 304.57 | 3.03 |
| 6 | Etoricoxib | 5-Chloro-3-(4-methanesulfonylphenyl)-6'-methyl-[2,3']bipyridinyl | 358.84 | 294.24 | 345.4 | 2.78 |
| 6a | | 5-Chloro-3-(4-methanesulfonylphenyl)-3-(6-methylpyridin-3-yl)-2,3-dihydro-[1,3]azasiline | 376.93 | 298.36 | 350.75 | 3.08 |
| 6b | | 5-Chloro-2-(4-methanesulfonylphenyl)-2-(6-methylpyridin-3-yl)-2,3-dihydro-[1,2]azasiline | 376.93 | 301.91 | 356.09 | 3.34 |

FIGURE 8A CONTINUED

| # | Common Name | IUPAC name | M.W. | Molecular Volume (Å³) | Molecular Surface (Å²) | Calculated Log P |
|---|---|---|---|---|---|---|
| 7 | | 6-Ethoxy-4-(4-fluorophenyl)-3-(4-methanesulfonylphenyl)-pyran-2-one | 388.41 | 316.96 | 369.96 | 2.24 |
| 7a | | 6-Ethoxy-4-(4-fluorophenyl)-3-(4-methanesulfonylphenyl)-3,4-dihydro-[1,3]oxasilin-2-one | 406.50 | 321.95 | 371.67 | 2.83 |
| 7b | | 6-Ethoxy-4-(4-fluorophenyl)-3-(4-methanesulfonylphenyl)-3,4-dihydro-[1,4]oxasilin-2-one | 406.50 | 323.66 | 381.62 | 2.82 |
| 8 | | 6-Ethylsulfanyl-3-(4-methanesulfonylphenyl)-4-phenyl-pyran-2-one | 386.49 | 322.67 | 375.62 | 2.95 |
| 8a | | 6-Ethylsulfanyl-3-(4-methanesulfonylphenyl)-3-phenyl-3,4-dihydro-[1,3]oxasilin-2-one | 404.58 | 327.82 | 377.99 | 3.59 |
| 8b | | 6-Ethylsulfanyl-4-(4-methanesulfonylphenyl)-4-phenyl-3,4-dihydro-[1,4]oxasilin-2-one | 404.58 | 330.20 | 388.04 | 3.51 |
| 9 | | 4-(4-Butylphenyl)-5-(4-methanesulfonylphenyl)-2,2-dimethyl-furan-3-one | 398.52 | 363.33 | 432.66 | 3.24 |
| 9a | | 4-(4-Butylphenyl)-5-(4-methanesulfonylphenyl)-2,2-dimethyl-[1,2]oxazasilol-3-one | 414.59 | 369.08 | 439.82 | 3.93 |
| 9b | | 4-(4-Butylphenyl)-2-(4-methanesulfonylphenyl)-5,5-dimethyl-[1,2]oxasilolan-4-one | 416.61 | 372.22 | 444.28 | 3.56 |
| 9c | | 5-(4-Butylphenyl)-5-(4-methanesulfonylphenyl)-2,2-dimethyl-[1,2,5]oxadisilolan-3-one | 432.69 | 377.99 | 455.43 | 4.06 |
| 10 | | 3-[1-(4-Methanesulfonylphenyl)-4-trifluoromethyl-1H-imidazol-2-yl]-pyridine | 367.35 | 275.44 | 326.64 | 2.39 |
| 10a | | 3-[1-(4-Methanesulfonylphenyl)-4-trimethylsilanyl-1H-imidazol-2-yl]-pyridine | 371.53 | 316.72 | 368.23 | 2.81 |
| 10b | | 3-[2-(4-Methanesulfonylphenyl)-4-trifluoromethyl-2H-[1,3,2]diazasilol-2-yl]-pyridine | 383.42 | 277.57 | 329.65 | 2.69 |

FIGURE 8A CONTINUED

| # | Common Name | IUPAC name | M.W. | Molecular Volume (Å³) | Molecular Surface (Å²) | Calculated Log P |
|---|---|---|---|---|---|---|
| 11 | | 1-(4-Methanesulfonylphenyl)-2-phenyl-4-trifluoromethyl-1H-imidazole | 366.36 | 279.89 | 332.41 | 3.25 |
| 11 a | | 1-(4-Methanesulfonylphenyl)-2-phenyl-4-trimethylsilanyl-1H-imidazole | 370.54 | 320.98 | 373.05 | 3.82 |
| 11 b | | 1-(4-Methanesulfonylphenyl)-2-phenyl-4-trifluoromethyl-2H-[1,3,2]diazasilole | 382.43 | 281.49 | 333.96 | 3.83 |

FIGURE 8B

Table 2. Results obtained from docking the compounds to COX-2 and COX-1 binding sites using respectively COX-2/Sc-558 and COX-1/Flurbiprofen as templates. Comparison of predicted versus experimental activities of the respective compounds toward both isoforms and of their selectivity for COX-2.

| # | Predicted $E_{bind}$ (Kcal/mol) for COX-2 | Experimental Activity: $pIC_{50}$, $-\log IC_{50}$ (COX-2) | Predicted Activity: $pIC_{50}$, $-\log IC_{50}$ (COX-2) | Predicted $E_{bind}$ (Kcal/mol) for COX-1 | Experimental Activity: $pIC_{50}$, $-\log IC_{50}$ (COX-1) | Predicted Activity: $pIC_{50}$, $-\log IC_{50}$ (COX-1) | Experimental selectivity index, log $pIC_{50}$ (COX-2) $-$ log $pIC_{50}$ (COX-1) | Predicted selectivity index, log $pIC_{50}$ (COX-2) $-$ log $pIC_{50}$ (COX-1) |
|---|---|---|---|---|---|---|---|---|
| 1 | −73.39 | 8.05 | 7.83 | −38.86 | 4.78 | 4.90 | 3.28 | 2.93 |
| 1a | −75.97 | | 8.08 | −25.12 | | 3.06 | | 5.02 |
| 1b | −63.82 | | 6.88 | −27.01 | | 3.32 | | 3.56 |
| 1c | −81.47 | | 8.63 | −25.03 | | 3.05 | | 5.58 |
| 1d | −65.22 | | 7.02 | −28.47 | | 3.51 | | 3.51 |
| 2 | −71.75 | 7.40 | 7.66 | −35.27 | 4.64 | 4.42 | 2.60 | 3.24 |
| 2a | −72.48 | | 7.74 | −22.83 | | 2.76 | | 4.98 |
| 2b | −66.92 | | 7.19 | −22.31 | | 2.69 | | 4.50 |
| 2c | −80.27 | | 8.51 | −22.06 | | 2.65 | | 5.86 |
| 2d | −68.47 | | 7.34 | −31.11 | | 3.86 | | 3.47 |
| 3 | −72.94 | 7.58 | 7.78 | −30.03 | 3.00 | 3.72 | 4.58 | 4.06 |
| 3a | −67.23 | | 7.22 | −12.34 | | 1.35 | | 5.87 |
| 3b | −69.91 | | 6.79 | −14.34 | | 1.62 | | 5.17 |
| 3c | −59.92 | | 6.50 | −15.75 | | 1.81 | | 4.69 |
| 3d | −64.51 | | 6.95 | −14.56 | | 1.65 | | 5.29 |
| 3e | −66.68 | | 7.17 | −13.84 | | 1.56 | | 5.61 |
| 4 | −68.88 | 7.40 | 7.38 | −21.51 | 2.96 | 2.58 | 4.45 | 4.80 |
| 4a | −71.55 | | 7.65 | −19.35 | | 2.29 | | 5.36 |
| 4b | −73.11 | | 7.80 | −21.72 | | 2.61 | | 5.19 |
| 4c | −63.12 | | 6.81 | −19.76 | | 2.35 | | 4.46 |
| 4d | −75.05 | | 7.99 | −25.89 | | 3.17 | | 4.82 |
| 5 | −72.51 | 7.52 | 7.74 | −35.11 | 4.45 | 4.42 | 3.07 | 3.32 |
| 5a | −67.04 | | 7.20 | −28.62 | | 3.54 | | 3.66 |
| 5b | −69.50 | | 7.44 | −14.79 | | 1.68 | | 5.76 |
| 5c | −72.08 | | 7.70 | −33.06 | | 4.13 | | 3.57 |
| 6 | −71.94 | 7.15 | 7.69 | −38.48 | 4.85 | 4.85 | 2.30 | 2.84 |
| 6a | −73.35 | | 7.82 | −36.81 | | 4.63 | | 3.19 |
| 6b | −79.72 | | 8.45 | −49.69 | | 6.35 | | 2.10 |
| 7 | −64.50 | 7.00 | 6.95 | −30.08 | 3.54 | 3.73 | 3.46 | 3.22 |
| 7a | −65.25 | | 7.02 | −18.24 | | 2.14 | | 4.88 |

FIGURE 8B CONTINUED

| # | Predicted $E_{bind}$ (Kcal/mol) for COX-2 | Experimental Activity: $pIC_{50}$ – $logIC_{50}$ (COX-2) | Predicted Activity: $pIC_{50}$ – $logIC_{50}$ (COX-2) | Predicted $E_{bind}$ (Kcal/mol) for COX-1 | Experimental Activity: $pIC_{50}$ – $logIC_{50}$ (COX-1) | Predicted Activity: $pIC_{50}$ – $logIC_{50}$ (COX-1) | Experimental selectivity index, log $pIC_{50}$ (COX-2) – log $pIC_{50}$ (COX-1) | Predicted selectivity index, log $pIC_{50}$ (COX-2) – log $pIC_{50}$ (COX-1) |
|---|---|---|---|---|---|---|---|---|
| 7b | −61.36 | | 6.64 | −46.74 | | 5.95 | | 0.69 |
| 8 | −72.96 | 8.49 | 7.79 | −26.85 | 3.40 | 3.30 | 5.09 | 4.49 |
| 8a | −74.37 | | 7.93 | −14.62 | | 1.66 | | 6.27 |
| 8b | −50.95 | | 5.61 | −29.97 | | 3.71 | | 1.90 |
| 9 | −76.40 | 8.30 | 8.13 | −32.23 | 4.90 | 4.02 | 3.40 | 4.11 |
| 9a | −73.63 | | 7.85 | −22.19 | | 2.67 | | 5.18 |
| 9b | −63.40 | | 6.84 | −32.41 | | 4.04 | | 2.80 |
| 9c | −72.63 | | 7.75 | −28.47 | | 3.51 | | 4.24 |
| 10 | −62.19 | 6.77 | 6.72 | −26.35 | 3.07 | 3.23 | 3.70 | 3.49 |
| 10a | −70.50 | | 7.54 | −15.23 | | 1.74 | | 5.80 |
| 10b | −60.71 | | 6.58 | −27.25 | | 3.35 | | 3.23 |
| 11 | −62.33 | 6.88 | 6.74 | −28.42 | 3.10 | 3.51 | 3.78 | 3.23 |
| 11a | −65.94 | | 7.09 | −15.12 | | 1.73 | | 5.36 |
| 11b | −56.15 | | 6.12 | −20.16 | | 2.40 | | 3.72 |

… # SILICON CONTAINING COMPOUNDS HAVING SELECTIVE COX-2 INHIBITORY ACTIVITY AND METHODS OF MAKING AND USING THE SAME

CROSS-REFERENCE TO RELATED APPLICATIONS

This application claims priority under 35 U.S.C. § 119(e) to U.S. Provisional Application Ser. No. 60/654,174 filed on Feb. 18, 2005; the disclosure of which is herein incorporated by reference.

INTRODUCTION

Background of the Invention

The many physiological roles of prostaglandins (PGs) are now fully recognized. In particular, they exert cytoprotective effects on the gastric mucosa and are critical for normal renal function [1]. Moreover, they trigger inflammation and the inhibition of their synthesis at inflammatory sites constitutes one of the best approaches to control inflammation [2]. PG $H_2$ is produced by the catalytic conversion of arachidonic acid by cyclooxygenase (PG endoperoxide $H_2$ synthetase, COX) isoforms 1 and 2, as a first step in PG synthesis [3].

COX-1 is constitutively expressed and is considered to be responsible for the physiological roles of PGs. In contrast, COX-2 is induced by mitogenic and pro-inflammatory stimuli [4] and induces undesired effects at inflammatory sites, such as pain. Classical non-steroidal antiinflammatory drugs (NSAIDs) like aspirin and ibuprofen non-selectively target both isoforms of the enzyme and consequently, long-term users develop undesirable side effects including gastric membrane degradation and renal failure [5].

Many efforts are therefore spent on the design of selective COX-2 inhibitors as NSAIDs with significantly reduced side effects. More recently, COX-2 has also been suggested to play a significant role in tumor angiogenesis and selective inhibitors have been proposed as antiangiogenic agents [6]. Selectivity in COX-2 inhibition by NSAIDs constitutes therefore an increasingly interesting challenge of current drug design.

Like aspirin, many early developed COX inhibitors such as indomethacin and flurbiprofen were found to bind at the active sites of both COX-1 and COX-2 with little specificity. As the overall structure of both COX isoforms is highly conserved, it took some time to identify the significant aspects of an inhibitor structure granting selectivity for COX-2, which was made possible with the subsequent development of the bicyclic nimesulide [7]. During this period, many efforts were spent by pharmaceutical laboratories to model, synthesize and assess the selectivity of several tricyclic compounds for COX-2 inhibition, as it was found that the binding site of the latter isoform was larger than that of COX-1, due to an Ile-Val substitution at residue 523 [7]. The shorter Val in COX-2 makes it indeed possible for compounds to reach an accessory secondary binding pocket, the entrance to which is restricted by the longer Ile side chain of COX-1. Many of these compounds were modeled after the tricyclic 1,5-diarylpyrazole Sc-558 (1) (FIG. (1)), which had earlier been used, along with the non selective flurbiprofen, to elucidate the structural bases for selective COX-2 inhibition by X-ray crystallography [8]. The development of this series of compounds led to the synthesis of the metabolically more labile Celecoxib (2) (FIG. (1)), which is nowadays a model of selective COX-2 inhibitors having reached the market [9]. That early development was based on the further derivatization of the 2,3-diaryl bromothiophene DuP 697, which was one of the original leads beside nimesulide [9]. This progressive and successful development of selective COX-2 inhibitors made ample use of classical bioisosteric replacements from the original lead such as CH/CF and $CH_2$/S/O, as exemplified by the Sc-558/Celecoxib series (FIG. (1)), and the Valdecoxib (4), Rofecoxib(5) and Etoricoxib (6) derivatives (FIG. (2)) that were subsequently developed [10-12]. Further developments led also to the replacement of the sulfonylamide and methanesulfonyl substituents by azido [13], sulfonylazide [14] and methanesulfonamide [15] bioisosteres, respectively yielding compounds with improved COX-2 selectivity.

However, despite the advances that have been made, there is continued interest the development of yet more selective COX-2 inhibitor compounds.

SUMMARY OF THE INVENTION

Silicon-containing compounds having selective COX-2 inhibitory activity, as well as compositions thereof are provided. The subject compounds find use in a variety of applications, including therapeutic applications. Also provided are kits containing the subject compounds and pharmaceutical preparations thereof.

BRIEF DESCRIPTIONS OF THE DRAWINGS

FIG. (1). Structures of the model compounds Sc-558 (1), Celecoxib (2) and Sc-57666 (3) used in the present study and of their sila-substituted derivatives (1a-d, 2a-d and 3a-e) compared for COX activity and selectivity.

FIG. (2). Structures of the-model compounds Valdecoxib (4), Rofecoxib (5), Etoricoxib (6) and two diarylpyran-2-ones (7 and 8) used in the present study and of their respective sila-substituted derivatives (4a-d, 5a-c, 6a-b, 7a-b and 8a-b) compared for COX activity and selectivity.

FIG. (3). Structures of the diarylfuran-3-one (9); and of the two diarylimidazoles (10 and 11) used as model compounds in the present study and of their respective sila-substituted derivatives (9a-c, 10a-b and 11a-b) compared for COX activity and selectivity.

FIG. (4). Superimposition of the docked structures 1 and 1c (ball and sticks) within the COX-2 binding site (residues in sticks). Hydrogens have been removed for clarity. The increased predicted activity of 1c (see Table 2) can be ascribed to a deeper penetration of the A ring within the accesssory secondary pocket resulting from the length of the Si—C bond with ring A, whilst the Si—C cycle rotation does not modify significantly the interactions within the primary pocket.

FIG. (5). Superimposition of the docked structures 6 and 6b (ball and sticks) within the COX-2 binding site (residues in sticks). Hydrogens have been removed for clarity. The increased predicted activity of 6b (see Table 2) can be ascribed to a deeper penetration of the A ring within the accesssory secondary pocket resulting from the length of the Si—C bond with ring A, whilst the Si—C cycle rotation does not modify significantly the interactions within the primary pocket.

FIG. (6). Superimposition of the docked structures 1 and 1c (ball and sticks) within the COX-1 binding site (residues in sticks). Hydrogens have been removed for clarity. The decreased predicted activity of 1c (see Table 2) can be ascribed to a loss of contact of the B ring with Tyr385, resulting from a decreased interaction of the C cycle $CF_3$ substituent with Ser530 due to the Si—C cycle rotation.

FIG. (7). Superimposition of the docked structures 6 and 6b (ball and sticks) within the COX-1 binding site (residues in sticks). Hydrogens have been removed for clarity. The increased predicted activity of 6b (see Table 2) can be ascribed to an increased contact of the B ring with Tyr385, resulting from an increased interaction of the C cycle Cl substituent with Ser530 due to the Si—C cycle rotation.

FIG. 8a provides Table 1, which is an Identification and physico-chemical characteristics of the model and sila-substituted compounds evaluated.

FIG. 8b provides Table 2, which provides results obtained from docking the compounds to COX-2 and COX-1 binding sites using respectively COX-2/Sc-558 and COX-1/Flurbiprofen as templates. Comparison of predicted versus experimental activities of the respective compounds toward both isoforms and of their selectivity for COX-2.

DEFINITIONS

Unless otherwise stated, the following terms used in the specification and claims have the meanings given below:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl, pentyl, and the like. "Alkenyl" means a linear monovalent hydrocarbon radical of two to six carbon atoms or a branched monovalent hydrocarbon radical of three to six carbon atoms containing at least one double bond, e.g., ethenyl, 2-propenyl, and the like.

"Alkynyl" means a linear monovalent hydrocarbon radical of two to six carbon atoms or a branched monovalent hydrocarbon radical of three to six carbon atoms containing at least one triple bond, e.g., ethynyl, propynyl, butynyl, and the like.

"Cycloalkyl" means a cyclic saturated monovalent hydrocarbon radical of three to seven carbon atoms, e.g., cyclopropyl, cyclohexyl, and the like.

"Halo" means fluoro, chloro, bromo, and iodo.

"aloalkyl" means alkyl substituted with one or more halogen atoms, including those substituted with different halogens, e.g., $-CH_2Cl$, $-CF_3$, $-CH_2CF_3$, $-CF_2CF_3$, $-CH_2CCl_3$, and the like.

"Alkoxy", "alkenyloxy", "cycloalkyloxy", or "haloalkyloxy" means a radical —OR where R is alkyl, alkenyl, cycloalkyl, or haloalkyl respectively as defined above, e.g., methoxy, ethoxy, propoxy, 2-propoxy, ethenyloxy, cyclopropyloxy, cyclobutyloxy, $-OCH_2Cl$, $-OCF_3$, and the like.

"Alkylthio" or "cycloalkylthio" means a radical —SR where R is alkyl or cycloalkyl respectively as defined above, e.g., methylthio, butylthio, cyclopropylthio, and the like.

"Acyl" means a radical —C(O)R where R is hydrogen, alkyl, or haloalkyl as defined above, e.g., formyl, acetyl, trifluoroacetyl, butanoyl, and the like.

"Amino" means a radical —$NH_2$, (1-methylethyl)amino, and the like.

"Disubstituted amino" means a radical —NRR' where R and R' are independently alkyl or acyl, e.g., dimethylamino, methylethylamino, di(1-methylethyl)amino, and the like.

"Hydroxyalkyl" means a linear monovalent hydrocarbon radical of two to six carbon atoms or a branched monovalent hydrocarbon radical of three to six carbons substituted with one or two hydroxy groups, provided that if two hydroxy groups are present they are not both on the same carbon atom. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4hydroxybutyl, 2,3-dihydroxypropyl, 1-(hydroxymethyl)-2-hydroxyethyl, 2,3-dihydroxybutyl, 3,4dihydroxybutyl and 2-(hydroxymethyl)-3-hydroxypropyl, 2-hydroxyethyl, 2,3-dihydroxypropyl, and 1-(hydroxymethyl)-2-hydroxyethyl.

"Alkoxyalkyl" means a linear monovalent hydrocarbon radical of one to six carbon atoms or a branched monovalent hydrocarbon radical of three to six carbons substituted with at least one alkoxy group as defined above, e.g., 2-methoxyethyl, 2-methoxypropyl, and the like.

"Hydroxyalkyloxy" or "alkoxyalkyloxy" means a radical-OR where R is hydroxyalkyl or alkoxyalkyl respectively as defined above, e.g., 2-hydroxyethyloxy, 2-methoxyethyloxy, and the like.

"Aminoalkyl" means a linear monovalent hydrocarbon radical of two to six carbon atoms or a branched monovalent hydrocarbon radical of three to six carbons substituted with at least one —NRR' where R and R' are independently selected from hydrogen, alkyl, or acyl, e.g., 2-aminoethyl, 2-N,N-diethylaminopropyl, 2-N-acetylaminoethyl, and the like.

"Aryl" means a monovalent monocyclic or bicyclic aromatic hydrocarbon radical of 6 to 12 ring atoms, and optionally substituted independently with one or more substituents selected from alkyl, haloalkyl, cycloalkyl, alkoxy, alkylthio, halo, nitro, acyl, cyano, amino, monosubstituted amino, disubstituted amino, -hydroxy, carboxy, or alkoxycarbonyl. Representative examples include, but are not limited to, phenyl, biphenyl, 1-naphthyl, and 2-naphthyl and the derivatives thereof.

"Heteroaryl" means a monovalent monocyclic or bicyclic aromatic radical of 5 to 10 ring atoms containing one or more, sometimes one or two ring heteroatoms selected from N, O, or S, the remaining ring atoms being C. The heteroaryl ring is optionally substituted independently with one or more substituents, sometimes one or two substituents, selected from alkyl, haloalkyl, cycloalkyl, alkoxy, alkylthio, halo, nitro, acyl, cyano, amino, monosubstituted amino, disubstituted amino, hydroxy, carboxy, or alkoxycarbonyl. Specifically the term heteroaryl includes, but is not limited to, pyridyl, pyrrolyl, thienyl, furanyl, indolyl, quinolyl, benzopyranyl, and thiazolyl, and the derivatives thereof.

"Heterocycloamino" means a saturated monovalent cyclic group of 3 to 8 ring atoms, wherein at least one ring atom is N and optionally contains a second ring heteroatom selected from the group consisting of N, O, or $S(O)_n$ (where n is an integer from 0 to 2), the remaining ring atoms being C. The heterocycloamino ring may be optionally fused to a benzene ring or it may be optionally substituted independently with one or more substituents, sometimes one or two substituents, selected from alkyl, haloalkyl, cycloalkyl, cycloalkylalkyl, aryl, aralkyl, heteroaryl, heteroaralkyl, halo, cyano, acyl, amino, monosubstituted amino, disubstituted amino, carboxy, or alkoxycarbonyl. More specifically the term heterocycloamino includes, but is not limited to, pyrrolidino, piperidino, morpholino, piperazino, indolino, and thiomorpholino, and the derivatives thereof.

"Heterocyclo" means a saturated monovalent cyclic group of 3 to 8 ring atoms in which one or two ring atoms are heteroatoms selected from N, O, or $S(O)_n$, where n is an integer from 0 to 2, the remaining ring atoms being C. The heterocyclo ring may be optionally fused to a benzene ring or it may be optionally substituted independently with one or more substituents, sometimes one or two substituents, selected from alkyl, haloalkyl, cycloalkyl, cycloalkylalkyl, aryl, aralkyl, heteroaralkyl, halo, cyano, acyl, monosubstituted amino, disubstituted amino, carboxy, or alkoxycarbonyl. More specifically the term heterocyclo includes, but is not limited to, pyrrolidino, piperidino, morpholino, piperazino, tetrahydropyranyl, and thiomorpholino, and the derivatives thereof.

"Cycloalkylalkyl" means a radical —$R^a R^b$ where $R^a$ is an alkylene group and $R^b$ is a cycloalkyl group as defined above e.g., cyclopropylmethyl, cyclohexylpropyl, 3-cyclohexyl-2-methylpropyl, and the like.

"Cycloalkylalkyloxy" means a radical —OR where R is a cycloalkylalkyl group as defined above e.g., cyclopropylmethyloxy, 3-cyclohexylpropyloxy, and the like.

"Aralkyl" means a radical —$R^a R^b$ where $R^a$ is an alkylene group and $R^b$ is an aryl group as defined above e.g., benzyl, phenylethyl, 3-(3-chlorophenyl)-2-methylpentyl, and the like.

"Heteroaralkyl" means a radical —$R^a R^b$ where $R^a$ is an alkylene group and $R^b$ is a heteroaryl group as defined above e.g., 2-, 3-, or 4-pyridylmethyl, furan-2-ylmethyl and the like.

"Heterocycloalkyl" means a radical —$R^a R^b$ where $R^a$ is an alkylene group and $R^b$ is a heterocyclo group as defined above e.g., morpholin-4-ylethyl, tetrahydrofuran-2-ylmethyl and the like.

"Pro-drugs" means any compound which releases an active parent drug according to formula (I) in vivo when such pro-drug is administered to a mammalian subject. Prodrugs of a compound of formula (I) are prepared by modifying functional groups present in the compound of formula (I) in such a way that the modifications may be cleaved in vivo to release the parent compound. Prodrugs include compounds of formula (I) wherein a hydroxy, amino, or sulfhydryl group in compound (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of formula (I), and the like.

"Optional" or "optionally" means that the subsequently described event or circumstance may, but need not, occur, and that the description includes instances where the event or circumstance occurs and instances in which it does not. For example, "heterocyclo group optionally mono-or di-substituted with an alkyl group" means that the alkyl may, but need not, be present, and the description includes situations where the heterocyclo group is mono-or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R-and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The compounds of this invention may possess one or more asymmetric centers; such compounds can therefore be produced as individual (R)-or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. "A pharmaceutically acceptable excipient" as used in the specification and claims includes both one and more than one such excipient.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4methylbicyclo-2,2,2'oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

DESCRIPTION OF THE SPECIFIC EMBODIMENTS

Silicon-containing compounds having selective COX-2 inhibitory activity, as well as compositions thereof are provided. The subject compounds find use in a variety of applications, including therapeutic applications. Also provided are kits containing the subject compounds and pharmaceutical preparations thereof.

Before the present invention is further described, it is to be understood that this invention is not limited to particular embodiments described, as such and may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In further describing the subject invention, the subject silicon-containing compounds having selective COX-2 inhibitory activity are described first in greater detail, followed by a review of various methods of producing the subject compounds as well as representative applications in which the subject compounds find use.

Silicon-Containing Compounds Having Selective Cox-2 Inhibitory Activity

As summarized above, the invention provides silicon-containing compounds having selective COX-2 inhibitory activity. As the compounds have COX-2 inhibitory activity, they are properly referred to as COX-2 inhibitors. The terms "COX-2 inhibitor," "inhibitor of cyclooxygenase-2" and "cyclooxygenase-2 inhibitor" as used herein embrace compounds which selectively inhibit cyclooxygenase-2 over cyclooxygenase-1. As such, the compounds are also properly referred to as compounds having selective COX-2 inhibitory activity. Employing the human whole blood COX-1 assay and the human whole blood COX-2 assay described in C. Brideau et al, Inflamm. Res. 45: 68-74 (1996), representative compounds of the invention have a cyclooxygenase-2 $IC_{50}$ of less than about 2 μM in the human whole blood COX-2 assay, yet have a cyclooxygenase-1 $IC_{50}$ of greater than about 5 μM in the human whole blood COX-1 assay. Also preferably, the compounds have a selectivity ratio of cyclooxygenase-2 inhibition over cyclooxygenase-1 inhibition of at least about 1.5 or more, and including at least 3.5 or more as determined using the protocols described in the Experimental section, below.

In representative embodiments, the compounds are non-steroidal anti-inflammatory drugs that exhibit anti-inflammatory, analgesic and antipyretic effects. In representative embodiments, the compounds are small molecules, where in representative embodiments the compounds have a molecular weight ranging from about 150 to about 1000 daltons, including from about 200 to about 800 daltons, such as from about 250 to about 500 daltons. In representative embodiments, the compounds having a molecular volume ranging from about 200 to about 500, such as from about 250 to about 380 $Å^3$, and a molecular surface area ranging from about 300 to about 500, including from about 307 to about 455 $Å^2$.

In the broadest sense, the silicon containing compounds may have any structure, so long as they exhibit selective COX-2 inhibitory activity, as reviewed above. In representative embodiments, the subject silicon-containing compounds are silicon containing derivatives of known COX-2 inhibitor compounds, including silicon containing analogs, homologs, isosteres, etc., of known COX-2 inhibitor compounds. As explained in J. Talley, Exp. Opin. Ther. Patents (1997), 7(1), pp. 55-62, three distinct structural classes of selective COX-2 inhibitor compounds have been identified. One class is the methane sulfonanilide class of inhibitors, of which NS-398, flosulide, nimesulide and L-745,337 are example members.

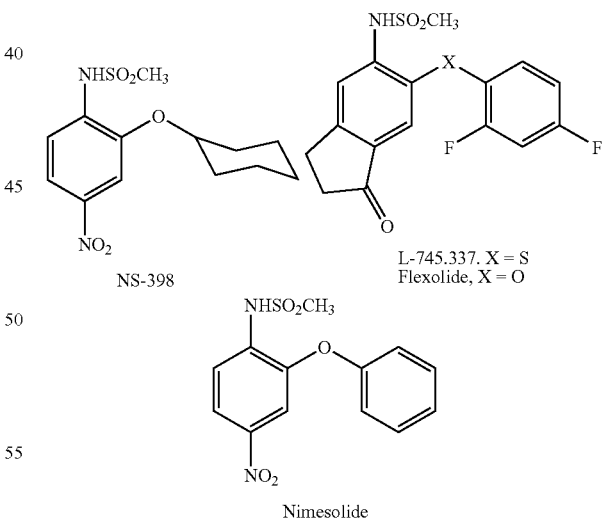

A second class is the tricyclic inhibitor class, which can be further divided into the sub-classes of tricyclic inhibitors with a central carbocyclic ring (examples include SC-57666, 1, and 2); those with a central monocyclic heterocyclic ring (examples include DuP 697, SC-58125, SC-58635, and 3, 4 and 5); and those with a central bicyclic heterocyclic ring (examples include 6, 7, 8, 9 and 10). Compounds 3, 4 and 5 are described in U.S. Pat. No. 5,474,995.

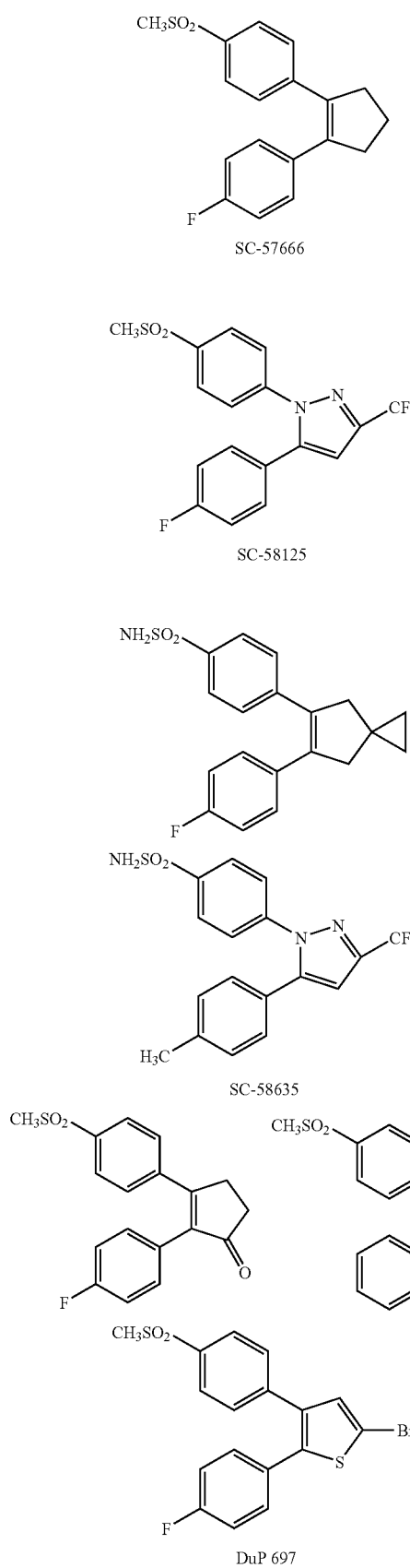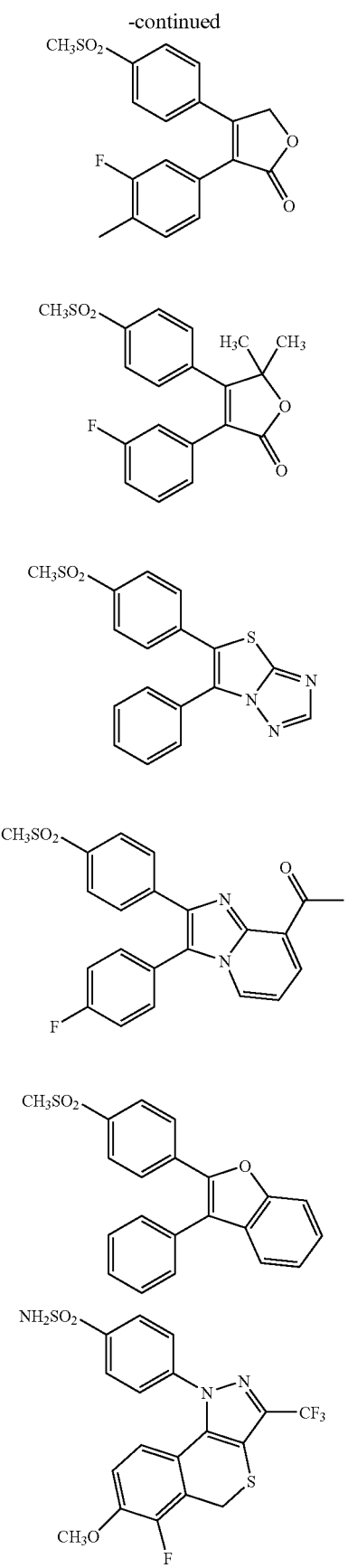

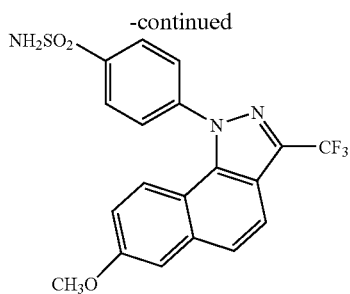

The third identified class can be referred to as those which are structurally modified NSAIDS, and includes L-761,066 and structure 11 as example members.

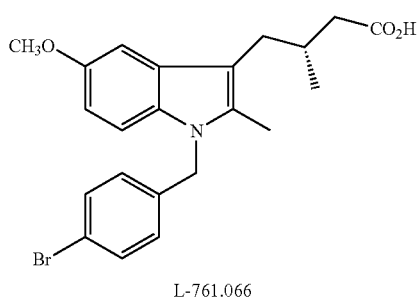

L-761.066

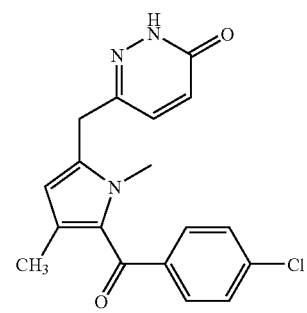

In addition to the structural classes, sub-classes, specific COX-2 inhibitor compound examples, and reference journal and patent publications described in the Talley publication, examples of compounds which selectively inhibit cyclooxygenase-2 have also been described in the following patent publications, all of which are herein incorporated by reference: U.S. Pat. Nos. 5,344,991, 5,380,738, 5,393,790, 5,409,944, 5,434,178, 5,436,265, 5,466,823, 5,474,995, 5,510,368, 5,536,752, 5,550,142, 5,552,422, 5,604,253, 5,604,260, 5,639,780; and International Patent Specification Nos. 94/13635, 94/15932, 94/20480, 94/26731, 94/27980, 95/00501, 95/15316, 96/03387, 96/03388, 96/06840; and International Publication No.'s WO 94/20480, WO 96/21667, WO 96/31509, WO 96/36623, WO 97/14691, WO 97/16435. Additional known COX-2 inhibitor compounds include:

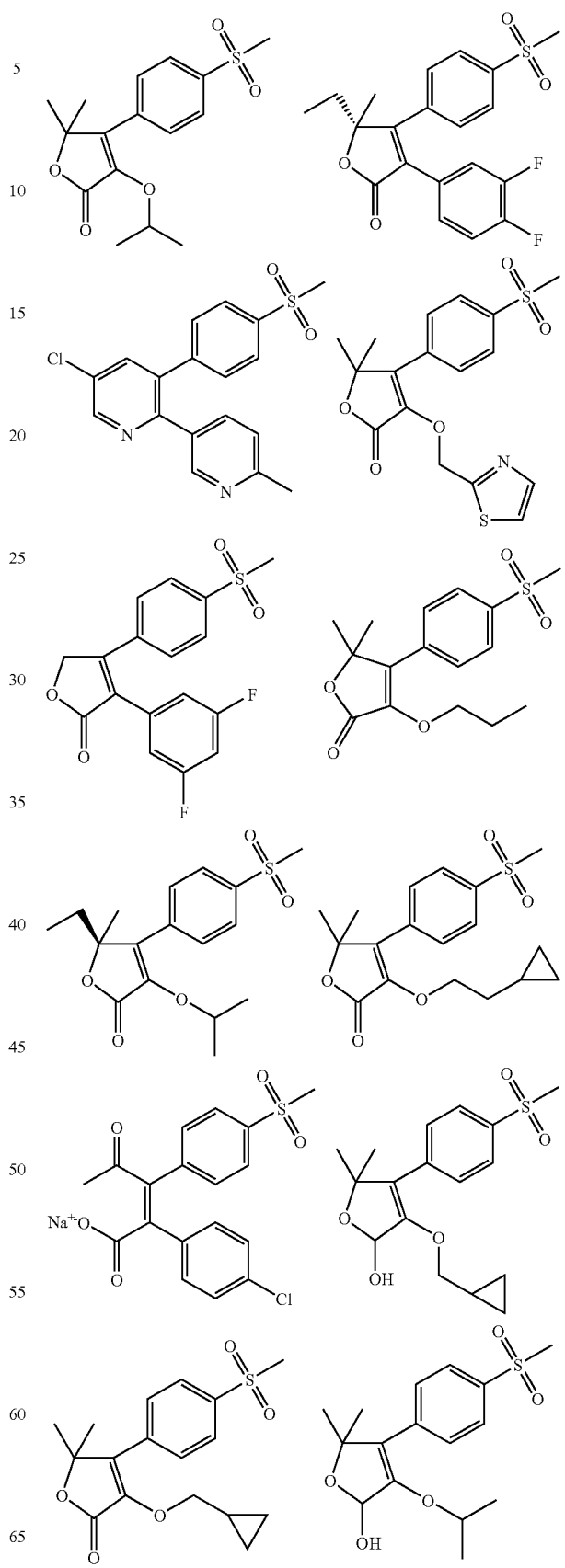

-continued

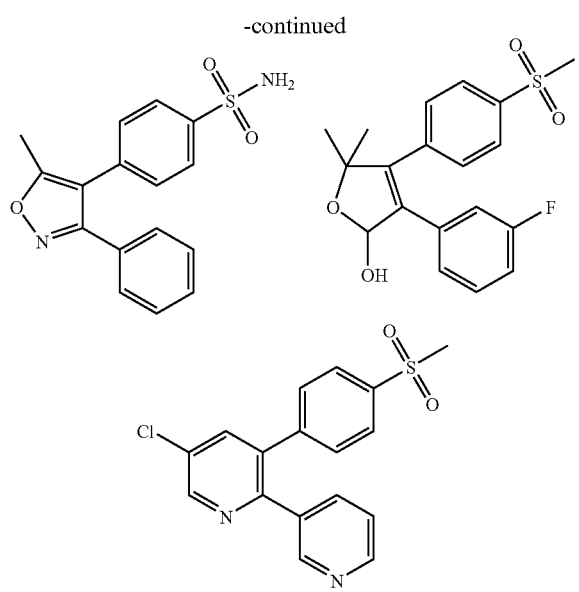

As the subject compounds are silicon-containing compounds, they include at least one silicon atom. The number of silicon atoms may range, in certain embodiments, from 1 to about 5, including from 1 to about 3, such as from 1 to 2.

Figure 2:
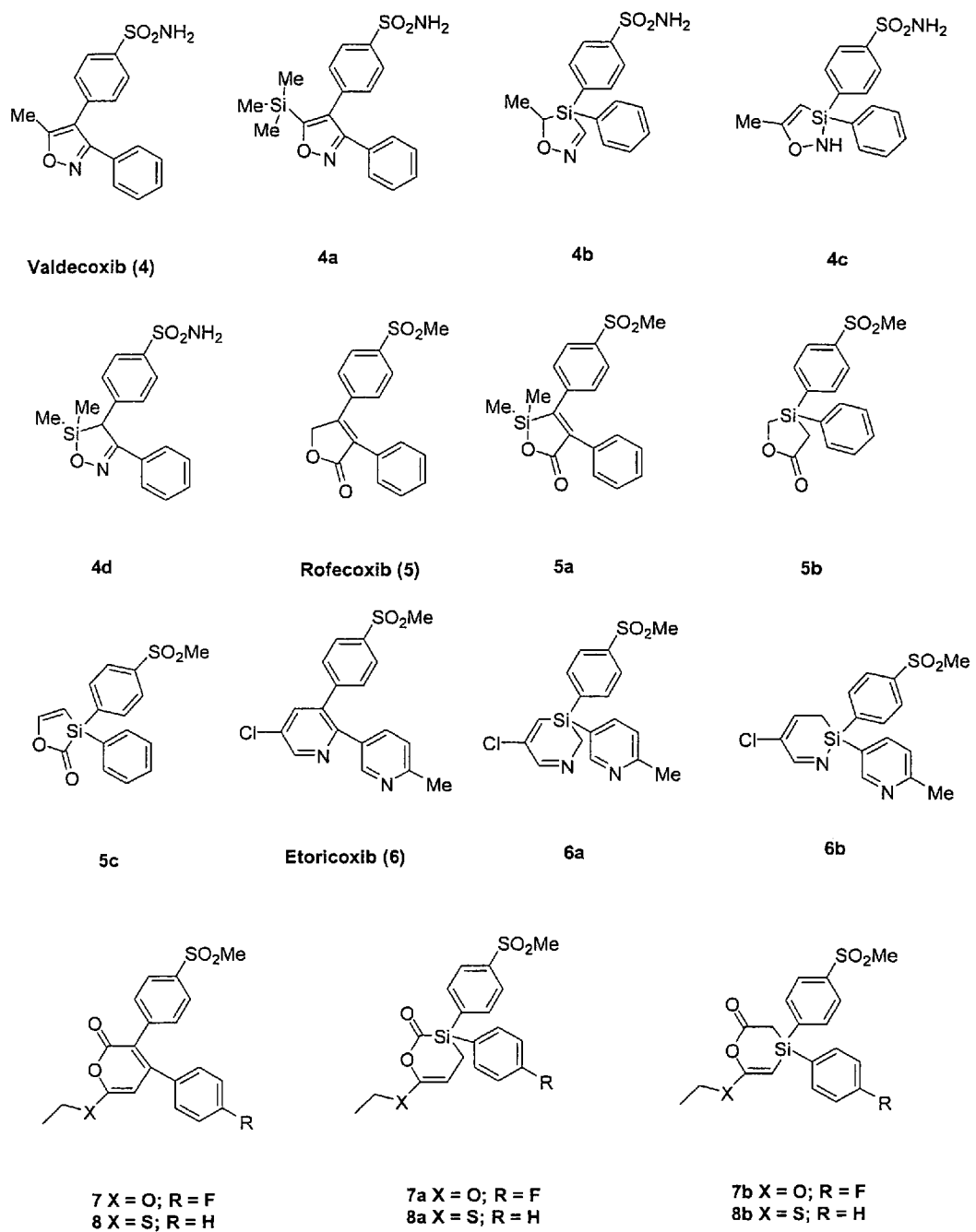
Figure 3:
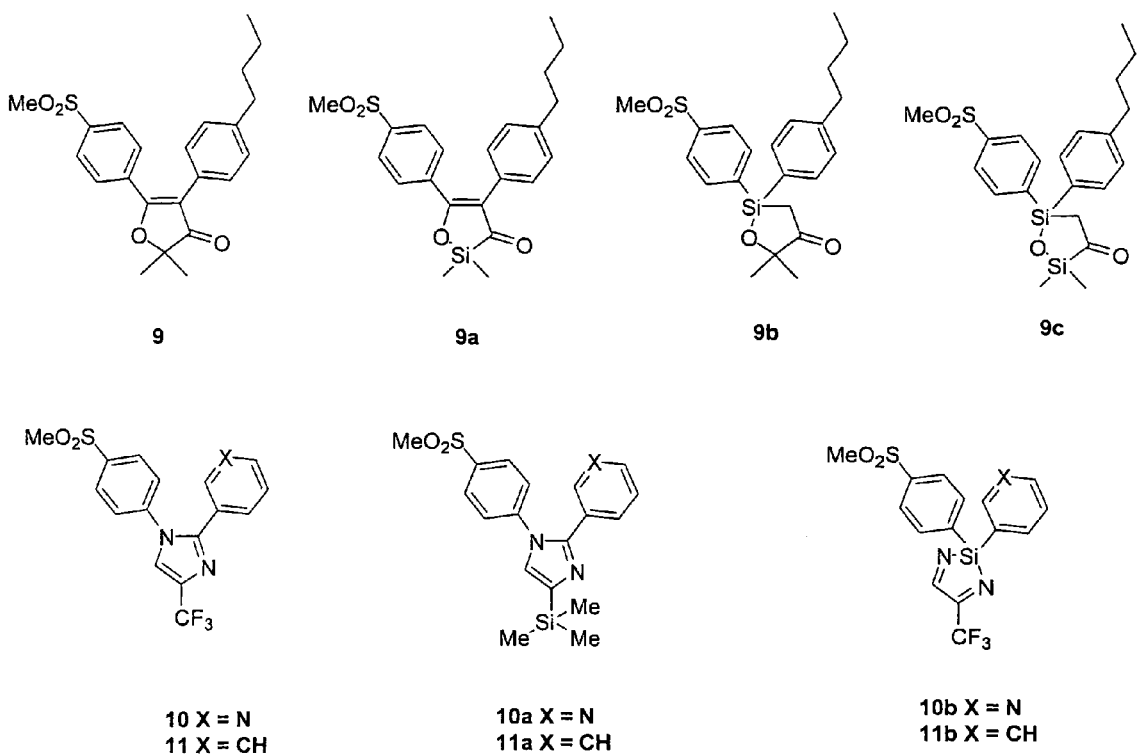
Figure 4:
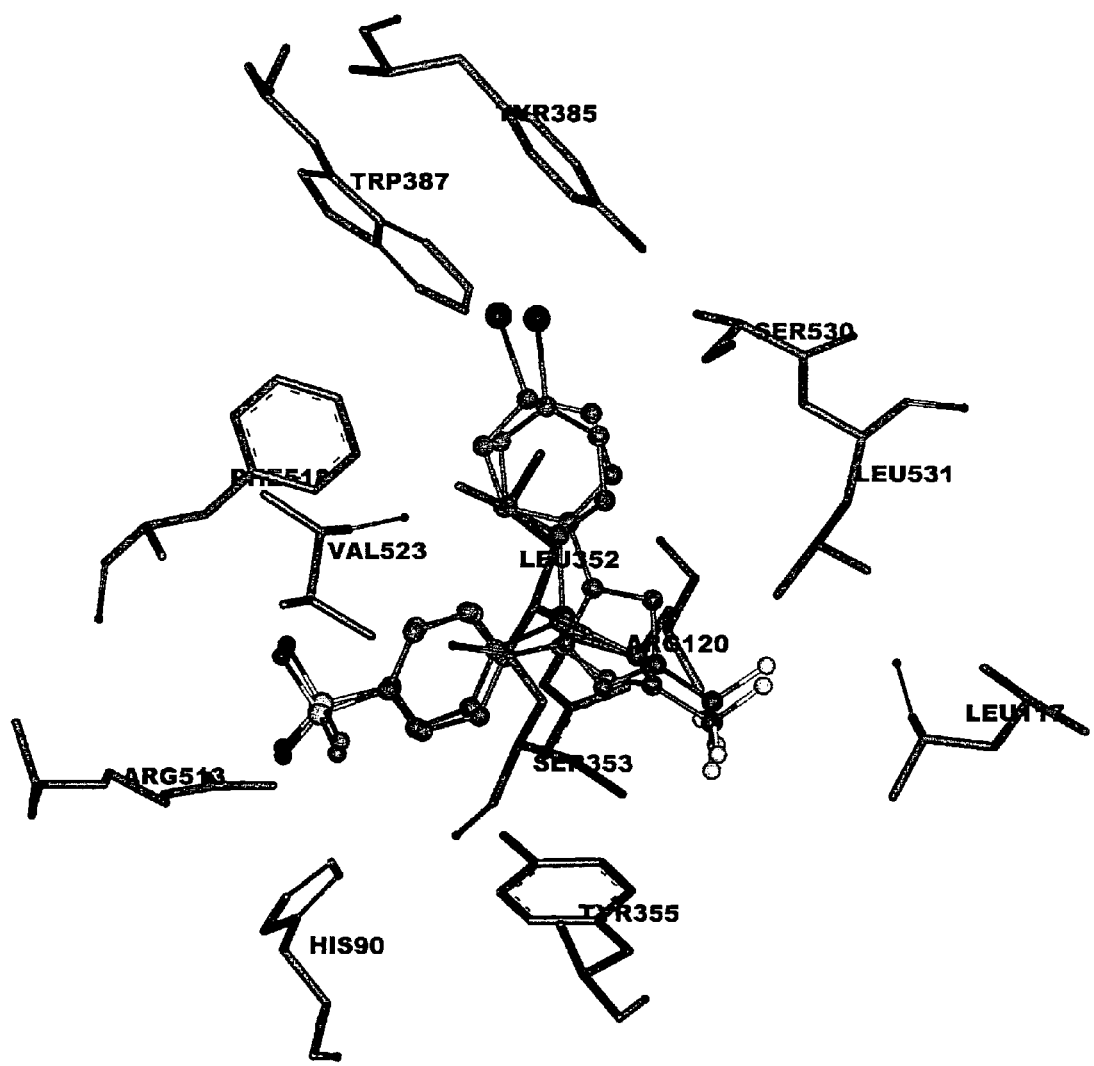
Figure 5:
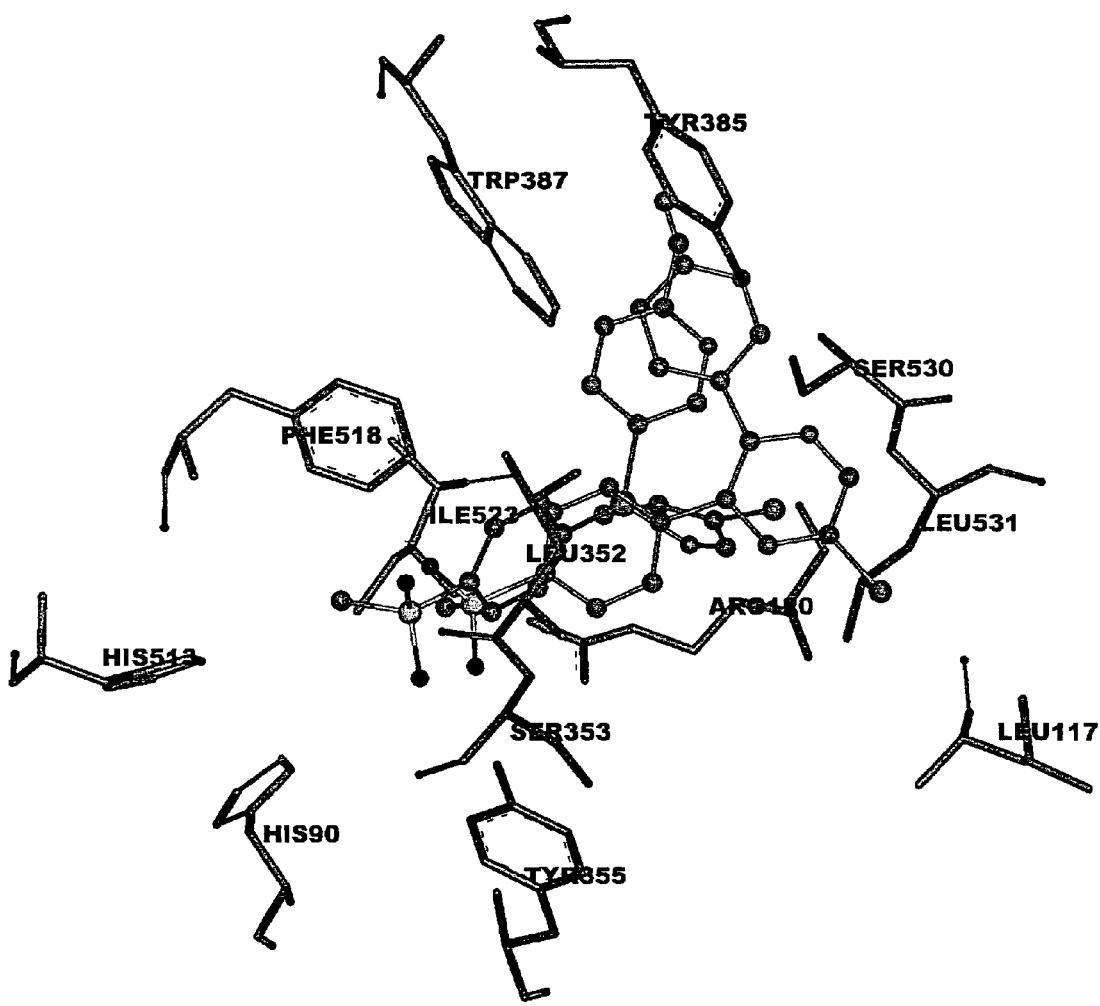
Figure 6:
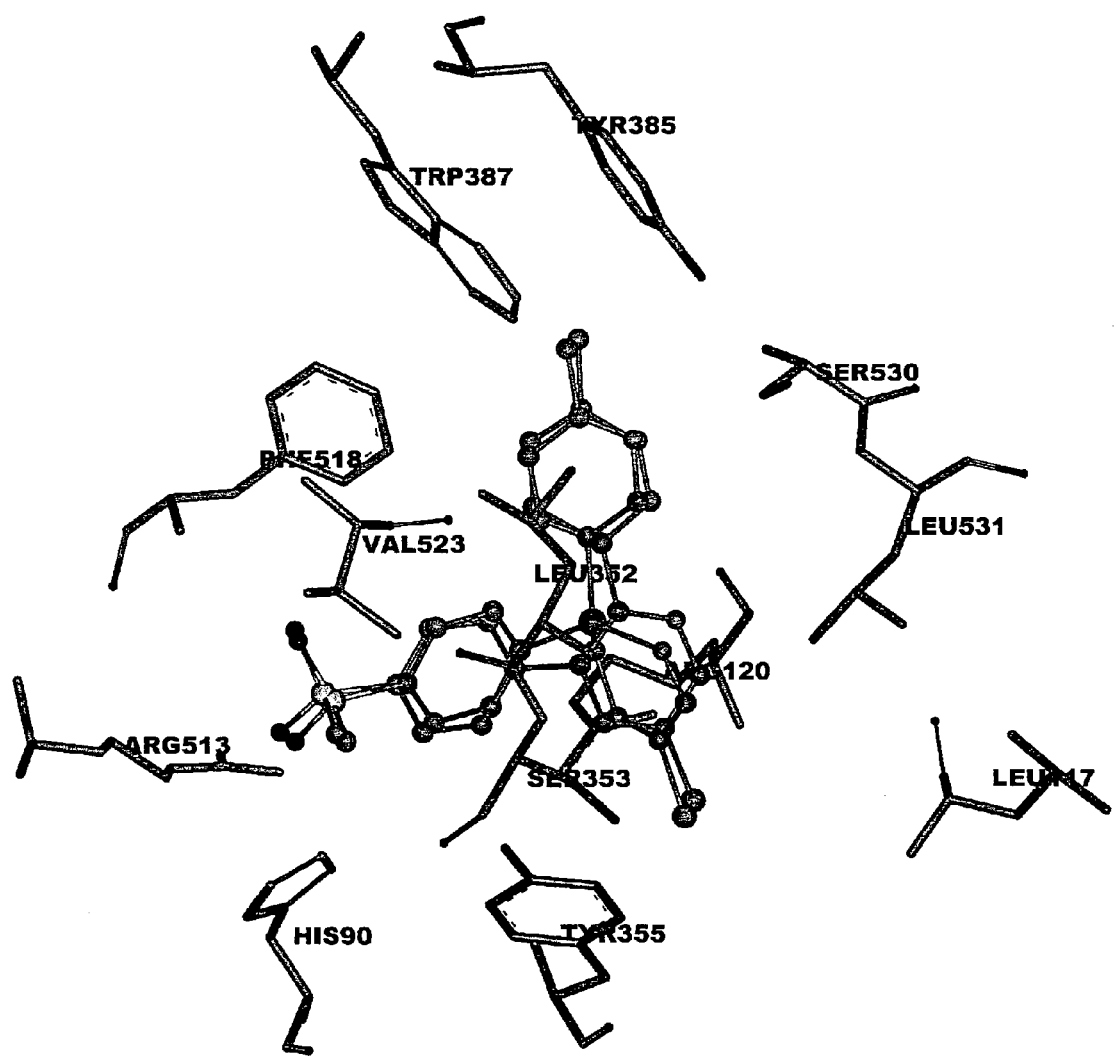
Figure 7:
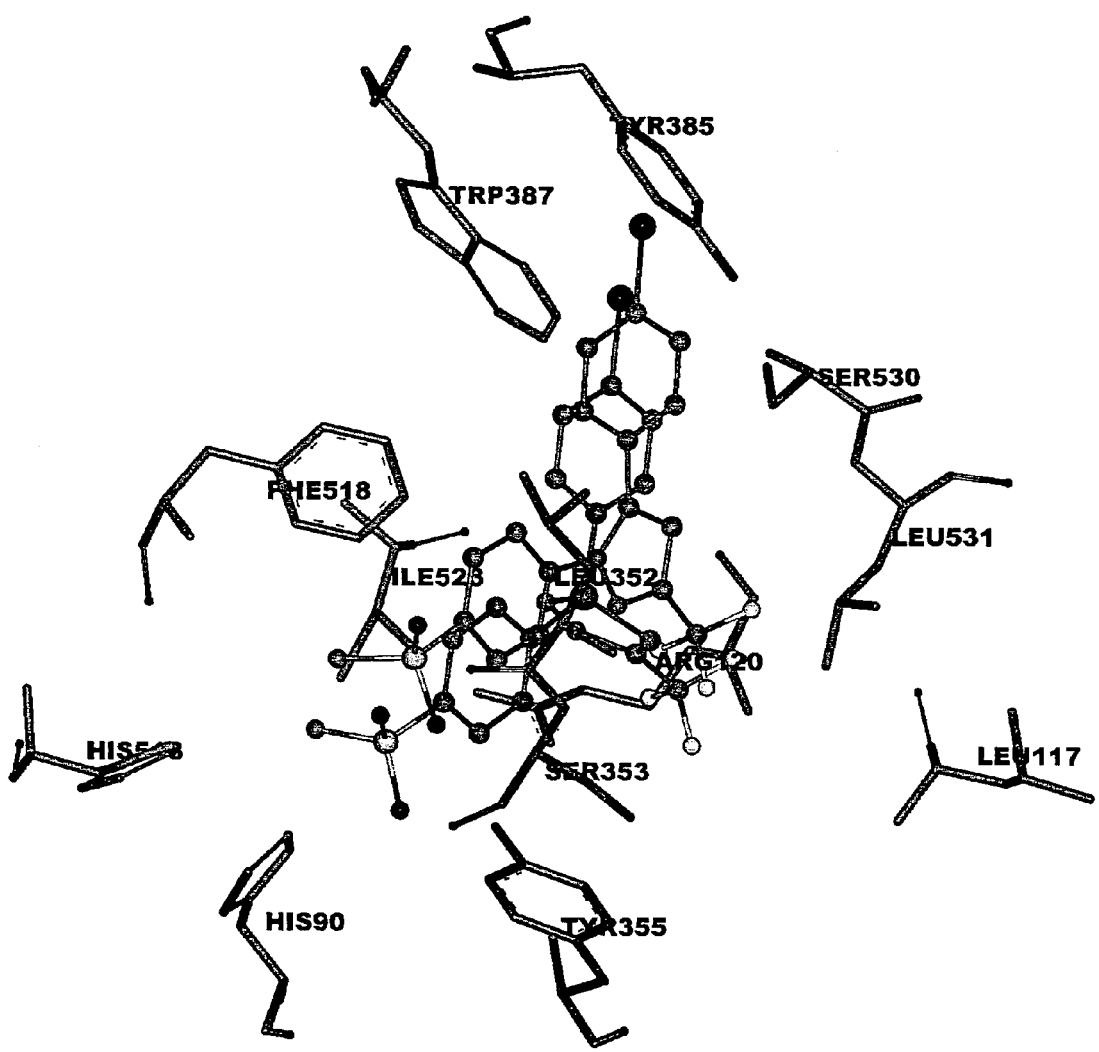

Specific representative silicon-containing compounds of the subject invention include, but are not limited to the silicon containing compounds shown in FIGS. 1, 2 and 3 and reported in Table 1, FIG. 8.

In certain embodiments, the compounds include at least one silicon containing substituent moiety. Representative members of this embodiment include compounds 1a, 2a, 4a, 10a and 11a.

In certain embodiments, the compounds include at least one annular silicon atom. Representative members of this embodiment include compounds 1b, 2b, 1c, 2c, 1d, 2d, 3a, 3b, 3c, 3d, 3e, 4b, 4c, 4d, 5a, 5b, 5c, 6a, 6b, 7a, 8a, 7b, 8b, 9a, 9b, 9c, 10b and 11b. In certain of these embodiments, at least one annular silicon atom is bonded to at least one phenyl substituent. Representative members of this embodiment include compounds 1b, 2b, 1c, 2c, 3d, 3e, 4b, 4c, 5b, 5c, 6a, 6b, 7a, 8a, 7b, 8b, 9b, 9c, 10b and 11b. In certain of these embodiments, at least annular silicon atom is bonded to at least two phenyl substituents. Representative members of this embodiment include compounds 1b, 2b, 1c, 2c, 3d, 3e, 4b, 4c, 5b, 5c, 6a, 6b, 7a, 8a, 7b, 8b, 9b, 9c, 10b and 11b.

The term COX-2 inhibitor includes all pharmaceutically acceptable salts for the COX-2 inhibiting compound selected. Also of interest are analogues of the compounds specified herein. Examples of such salt forms of COX-2 inhibitors include but are not limited to salts derived from inorganic bases including aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occuring substituted amines, cyclic amines, and basic ion exchange resins, such as arginine, betaine, caffeine, choline, N,N-dibenzylethylenediamine, diethylamide, 2-diethylaminoethanol, 2-dimethylaminoethanol, ethanolamine, ethylenediamine, N-ethylmorpholine, N-ethylpeperidine, glutamine, glucosamine, histidine, hydrabamine, isopropylamine, lysine, methyglucamine, morpholine, piperazine, piperidine, polyamine resins, procaine, purine, theobromine, triethylamine, trimethylamine, triporopylamine, troethamine, and the like.

Pharmaceutical Preparations

Also provided are pharmaceutical preparations of the subject compounds. The subject compounds can be incorporated into a variety of formulations for administration to a subject. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. The formulations may be designed for administration via a number of different routes, including oral, buccal, rectal, parenteral, intraperitoneal, intradermal, transdermal, intracheal, etc., administration.

In pharmaceutical dosage forms, the compounds may be administered in the form of their pharmaceutically acceptable salts, or they may also be used alone or in appropriate association, as well as in combination, with other pharmaceutically active compounds. The following methods and excipients are merely exemplary and are in no way limiting.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256, 108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethycellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

The compounds of this invention and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference in its entirety. Such patches may be constructed for continuous, pulsatile, or on demand delivery of pharmaceutical agents.

Optionally, the pharmaceutical composition may contain other pharmaceutically acceptable components, such a buffers, surfactants, antioxidants, viscosity modifying agents, preservatives and the like. Each of these components is well-known in the art. See, for example, U.S. Pat. No. 5,985,310, the disclosure of which is herein incorporated by reference.

Other components suitable for use in the formulations of the present invention can be found in Remington's Pharmaceutical Sciences, Mace Publishing Company, Philadelphia, Pa., 17th ed. (1985). In an embodiment, the aqueous cyclodextrin solution further comprise dextrose, e.g., about 5% dextrose.

Dosage levels of the order of from about 0.01 mg to about 140 mg/kg of body weight per day are useful in representative embodiments, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day. Those of skill will readily appreciate that dose levels can vary as a function of the specific compound, the severity of the symptoms and the susceptibility of the subject to side effects. Preferred dosages for a given compound are readily determinable by those of skill in the art by a variety of means.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

As such, unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier. The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular peptidomimetic compound employed and the effect to be achieved, and the pharmacodynamics associated with each compound in the host.

In certain embodiments, the compounds exhibit an increase in COX-1 inhibition whilst keeping a level of COX-2 inhibition similar to the parent compound, which compounds are, in certain embodiments, beneficial to a prevention of heart attacks. Representative embodiment of such compounds include compounds 6b and 8b.

Synthetic Methods

The subject compounds of the inventions may be synthesized using any convenient protocol or synthetic techniques. Representative synthetic approaches for representative compounds of the subject invention are provided in the Experimental Section, infra.

Utility

The subject compounds find utility in a variety of different applications, and in any application where selective COX-2 inhibitors find use. Representative applications include, but are not limited to therapeutic applications in which a subject is treated for a condition, e.g., a disease condition. By treatment is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

The subject compounds are useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis degenerative joint diseases (osteoarthritis), gout and ankylosing spondylitis, bursitis, burns, injuries, following surgical and dental procedures. In addition, the subject compounds may inhibit cellular neoplastic transformations and metastic tumor growth and hence can be used in the treatment of cancer. The subject compounds may also be useful for the treatment of dementia including pre-senile and senile dementia, and in particular, dementia associated with Alzheimer Disease (ie Alzheimer's dementia). The subject compounds, will also inhibit prostanoid-induced smooth muscle contraction by preventing the synthesis of contractile prostanoids and hence may be of use in the treatment of dysmenorrhea, premature labor and asthma. By virtue of their high cyclooxygenase-2 (COX-2) activity and/or its selectivity for cyclooxygenase-2 over cyclooxygenase-1 (COX-1) as defined above, the subject compounds are useful as an alternative to conventional non-steroidal antiinflammatory drugs (NSAID'S) particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems (including those relating to reduced or impaired platelet function); kidney disease (e.g. impaired renal function); those prior to surgery or taking anticoagulants; and those susceptable to NSAID induced asthma.

Similarly, the subject compounds are useful as a partial or complete substitute for conventional NSAIDs in preparations wherein they are presently co-administered with other agents or ingredients. Thus in further aspects, the invention encompasses pharmaceutical compositions for treating cyclooxygenase-2 mediated diseases as defined above comprising a non-toxic therapeutically effective amount of the subject compound as defined above and one or more ingredients such as another pain reliever including acetominophen or phenacetin; a potentiator including caffeine; an H2-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; a diuretic; a sedating or non-sedating antihistamine. In addition the invention encompasses a method of treating cyclooxygenase mediated diseases comprising: administration to a patient in need of such treatment a non-toxic therapeutically effect amount of the compound of the subject invention, optionally co-administered with one or more of such ingredients as listed immediately above.

Kits

Kits with unit doses of the compounds, usually in oral or injectable doses, are provided. For example, kits and systems for practicing the subject methods may include one or more pharmaceutical formulations.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation. The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

I. Chemistry

Selective COX-2 inhibitors are tricyclic compounds made of a central 5-or 6-membered cycle C (usually an heterocycle) substituted by two 6-membered rings (A and B) at adjacent positions. Phenyl ring A is further p-substituted by a sulfonylamide or a methanesulfonyl group and B is either a phenyl of an heteroaryl ring left unsusbtituted, or p-substituted by a methyl group or an halogen atom, respectively. A series of 11 compounds with different C cycles that have been extensively described in the literature were selected for the study (see FIGS. (1) to (3) for the structures). Beside the 1,5-diarylpyrazoles Sc-558 (1) and celecoxib (2) [9], Sc-57666 (3), an earlier 1,2-diarylcyclopentene, was also selected because of its high selectivity for COX-2 [20]. Other model compounds selected included the 3,4-diarylpyrazole Valdecoxib (4), the 3,4-diaryl-2-furanone Rofecoxib (5), the 4,5-diaryl-3-furanone (9) [21], the 3-phenyl-[2,3']bipyridinyl Etoricoxib (6), two 3,4-diarylpyran-2-ones (7 and 8) [22], and two 1,2-diarylimidazoles (10 and 11) [23]. The model compounds were imaginatively sila-substituted (see FIGS. (1) to (3)) whilst keeping in mind the possibilities offered by silicon synthetic chemistry. More specifically, three approaches were used. In the first approach (compounds 1a, 2a, 4a, 10a and 11a), the C cycle of the model compound was substituted by a trimethylsilanyl group in replacement of either the original methyl, or trifluoromethyl substituent. A silanyl substituent was not considered because it would be cleaved in water to form the corresponding silanol [16]. The regioselective silylation of aromatic C—H bonds has been reported in good yields by several groups, using respectively either ruthenium [24, 25] or nickel [26] derivatives as catalysts. In the second approach (compounds 1d, 2d, 3a-c, 4d, 5a and 9a), an intramolecular substitution was effected in cycle C of a carbon (usually the one substituted by a methyl or trifluoromethyl group in the model compound) by a dimethyl-substituted silicon atom. Finally, in the third approach (compounds 1b, 1c, 2b, 2c, 3d, 3e, 4b, 4c, 5b, 5c, 6a, 6b, 7a, 7b, 8a, 8b, 9b, 9c, 10b, and 11b), rings A and B were both attached to a silicon atom replacing either a carbon or a nitrogen atom (1b, 2b) of cycle C, so as to link both rings A and B together at one of their respective original positions in the model compounds. In support to the second and third approaches, it should be noted that various synthetic methodologies have been worked out to obtain in good yield dimethyl or diaryl 1,1-substituted siloles [27, 28] or silaheterocycles [29-32]. Such synthetic bioisosteric sila-substitutions in existing drugs have been pioneered in the last decade [16, 33] and are culminating nowadays with such complex structures as those of enantiomeric silicon-containing analogues of piperiden or difenidol, which are subtype-selective muscarinic receptor antagonists [34, 35], of sila-analogues of spiro[indane-1,4'-piperidines], which are selective dopamine and serotonine receptors ligands [36], or of the niguldipine calcium channel and $\alpha_1$-adrenoreceptor antagonists [37], respectively. The chemical names and physico-chemical characteristics of the compounds considered for this study are listed in Table 1.

II. Results and Discussion

The sila-substitution offers several advantages in drug design, inherent not only to the increased length of the Si—C versus C—C bond, but also to the physical characteristics of silicon [16]. The Si—C bond (1.87 Å) is increased by 20% when compared to the C—C bond (1.54 Å), which induces subtle changes in size and shape of a molecule. Such changes can be beneficial to the interaction with specific proteins of the silicon analogue in comparison to the carbon model counterpart. For instance, in dopamine and serotonine receptor ligands, a sila-substitution increases the affinity from 6-up to 37-fold [36], whilst in muscarinic receptor antagonists it results not only in an increased affinity, but also in an improvement of selectivity toward receptor subtypes [34, 35]. Silicon-containing analogues are also more lipophilic than their carbon counterparts. A small increase in drug lipophilicity results in a marked increase in its volume of distribution, and as a consequence the drug penetrates more deeply into tissues and is less prone to hepatic metabolism [16]. These potential advantages compelled the design of the present study intended to evaluate the theoretical application of the sila-substitution to selective COX-2 inhibitors. As expected, the replacement of a carbon by a silicon atom in these molecules (FIGS. (1) to (3)) induced changes in their physico-chemical characteristics (Table 1). Both volume and surface of the silicon-analogue molecules were increased versus their model compounds by 1-2% in most cases. The larger 15-20% increases in the trimethylsilanyl (1a, 2a, 4a, 10a and 11a) and the dimethylsilole compounds (1d, 2d, 3a-c, 4d and 5a) were the result of further methyl group additions. The calculated Log P (octanol/water) was also increased in most silicon derivatives (Table 1), reflecting their increased lipophilicity and hence the possible improvements in their tissue distribution [16].

With an aim at assessing the effects of C—Si replacements in the COX inhibitors on enzyme activity, the structures of the model and sila-substituted compounds were optimized for geometry and then docked with energy minimization in the respective binding sites of the two murine enzyme isoforms. As a control, the ligands originally present in the X-ray crystal structures used for the procedure (respectively Sc-558 (1) in COX-2 and flurbiprofen in COX-1) were reconstructed in Brookhaven protein data bank (pdb) format and docked in their respective emptied binding sites. The results generated docked structures with root mean square deviations (RMSD) between the two conformations of 0.05 Å for COX-2/Sc-558 and 0.09 Å for COX-1/flurbiprofen complexes, respectively. These results validate the parameter set used for docking as they indicate its appropriateness to reproduce the original X-ray structures [38]. The minimal energies of binding ($E_{bin}d$) calculated from the docking procedures with each of the model compounds (1-11, FIGS. (1)-(3)) were directly correlated to their respective experimental inhibitory activities found in the literature (expressed as $pIC_{50}=-\log IC_{50}$) toward both recombinant enzyme isoforms [8, 9, 10, 12, 14, 20, 21, 22, 23, 39, 40, 41]. Such a linear relationship between pIC$_{50}$ and binding energy was consistent with the results reported in another recent in silico study with COX-2 inhibitors [41]. The relationships observed in the present study (n=11) were respectively pIC$_{50}$ (COX-2)=0.582-0.098 E$_{bind}$ (Kcal/mol) and pIC$_{50}$ (COX-1)=−0.290-0.133 E$_{bind}$ (Kcal/mol), with squared correlation coefficients (r$^2$) of 0.66 for COX-2 and 0.75 for COX-1, respectively. The relatively good accuracy of these correlations further allowed us to predict the pIC$_{50}$ of the sila-substituted compounds for both COX isoforms. The selectivity of these inhibitors toward COX-2 is another important parameter, usually estimated by the ratio of COX-1 IC$_{50}$ over COX-2 IC$_{50}$. With the predicted pIC$_{50}$ data for both COX isoforms in hand, the selectivity of each compound for COX-2 could consequently be predicted. This parameter was expressed as the selectivity index, i.e. the log of the IC$_{50}$ ratio. A cross-validation of the predicted versus the experimental selectivity index obtained from the literature for the 11 model compounds provided a squared correlation coefficient q$^2$ of 0.64 and a standard error of prediction of 0.53, validating the accuracy of our predictions to ±15%. These results are summarized in Table 2.

In most cases, the sila-substitution did not improve significantly the predicted activity for COX-2, except in three instances where the predicted pIC$_{50}$ was increased by close to one log unit versus the corresponding model compound, namely the diaryldiazasiloles 1c and 2c, and the diarylazasiline 6b. In contrast, the predicted activity for COX-1 was significantly decreased for most of the sila-substituted compounds versus their respective model compounds, except in three cases, namely compounds 6b, 7b and 8b, where the predicted activity for COX-1 was significantly increased. These results are likely to emphasize the importance of the position on cycle C where rings A and B are simultaneously attached to the silicon atom. Indeed, the corresponding sila-substituted compounds 6a, 7a and 8a, in which the attachment position of both rings on cycle C is shifted from the original ring B substitution position to that of ring A (see FIG. (2)), see instead their predicted activity for COX-1 decreased. Noteworthy also is the significant decrease in predicted activity toward COX-1 observed for many sila-substituted compounds characterized by a poorly conjugated cycle C (e.g. 3a-e, 5b, 8a), although their predicted activity toward COX-2 remains as high as in their respective model compound. This suggests that the change in cycle C conformation induced by the introduction of a silicon atom might be less critical for maintaining COX-2 rather than COX-1 inhibitory activity.

Because the relative changes in activity toward both COX isoforms govern the selectivity for COX-2, it was also interesting to evaluate the possible impact on enzyme activity of the docked compounds geometry within the respective binding sites of COX-1 and COX-2. Amino acid sequences of COX-1 and COX-2 share 67% identity and the overall structures are highly conserved [8]. The COX active sites in the two isoforms are similar with a sequence identity of 87% and strict conservation [42]. Both isoforms contain a primary binding pocket with an accessory secondary pocket gated by Tyr355 and Val523 in COX-2, the latter being replaced by Ile523 in COX-1. The bulkier side chain of Ile523 in COX-1 restricts access of inhibitors to the secondary pocket, which the smaller side chain of Val523 allows in COX-2 [42]. This results in an enlargement of the binding site by 25%, with an available volume increasing from 316 Å$^3$ in COX-1 to 394 Å$^3$ in COX-2 [43, 44]. COX-2 selectivity is considered to be a consequence of preferential interactions of the inhibitor structure with two non-conserved residues within the accessory binding pocket of COX-2, namely Arg513 and Val523 [17]. In COX-1, these interactions occur with His513 and Ile523 and are much weaker [38]. However, other residues within the primary binding pocket have also been identified as critical for COX-2 selectivity. For instance, too strong a charge interaction of the C cycle substituent with Arg120 decreases the association rate of COX-2 inhibitors [45]. In contrast, the same C cycle substituent interacts preferentially with the hydroxyl group of Ser530 side chain of COX-1, which forces the ligand to adopt an alternative position in the primary binding pocket, the B ring being pushed into the hydrophobic hole at its top made by Tyr385 and Trp387 [17]. Increased activity for COX-1 is thus dependent on the strength of interaction of the B ring with Tyr385, on the decrease in the interaction of the C cycle substituent with Arg120, and on its resulting improved interaction with Ser530 [17, 44]. In selective COX-2 inhibitors, the loss of favorable B ring interaction with Tyr385 allows for the A ring to penetrate deeper into the accessory secondary binding pocket, which induces the sulfonamide or methanesulfonyl oxygens to establish H-bonds with Arg513 and His90, and the amido or methyl groups to interact with the hydrophobic chain made by Phe518, Leu352 and Ser353 [14, 38, 39, 41, 44, 46]. This is the result of strong van der Waals contacts of the C cycle substituent with Leu531 and Leu117 in the primary binding pocket [39, 41], although an H-bond remains possible with the hydroxyl group of Ser530 thanks to its specific rotation to a down-conformation in the COX-2 structure [44].

When examining the docked structures for interactions with the selected residues mentioned above, the advantages brought by the sila-substitution were found to result from changes in the distance of the inhibitor structure from these residues in the respective binding sites that were completely in line with the previous observations. Increased activity toward COX-2 was mainly governed by the depth with which ring A penetrates the secondary binding pocket of the isoform with increased H-bonding of the sulfonyl oxygens, particularly with His90. In contrast, increased activity toward COX-1 was primarily the consequence of an increased interaction of ring B with Tyr385 due to the strength of contact between the cycle C substituent and Ser530. The changes in activity of the sila-substituted compounds toward both enzyme isoforms and the resulting changes in selectivity for COX-2 as compared to the respective model compounds, are the consequence of the changes in bond lengths and bond angles due to the carbon-silicon replacement. This is best illustrated in FIGS. (4) to (7) with the docked structures of two extreme examples (see Table 2) presented by the respective compound pairs 1/1c and 6/6b. On the one hand, compound ic shows an increased predicted activity for COX-2 and a decreased predicted activity for COX-1, resulting in a predicted selectivity index for COX-2 that jumps from 2.93 to 5.58, when compared to the model Sc-558 (1). On the other hand, the similar increase in predicted activity toward COX-2 of compound 6b is matched by a strong increase of the predicted activity for COX-1, which results in a predicted selectivity index that drops slightly from 2.84 to 2.10, when compared to the model compound Etoricoxib (6).

The minimized structures of both sila-substituted 1c and 6b within the active site of COX-2 (FIGS. (4) and (5)) fit with those of their respective model compounds 1 and 6. Rings A and B are in similar planes whilst the Si—C substitution imparts a rotation to the cycle C plane by approximately 90°. But because the rotational angle leaves the respective CF$_3$ and Cl substituents close to their original orientation, this does not significantly alter the distances from, and hence the interactions with Leu117 and Leu531 within the primary pocket of the binding site. For instance, the distance of the respective CF₃ and Cl substituents from the —CH(CH₃)₂ side chain group of Leu117 change from 8.21 (1) to 8.25 Å (1c) and from 8.53 (6) to 8.88 Å (6b), respectively. The rotational angle of cycle C in the sila-substituted compounds removes however the same substituents from Arg120. The respective distances from the closer NH₂ of Arg120 change from 3.12 (1) to 3.37 Å (1c) and from 3.81 (6) to 4.24 Å (6b). The increased length of the Si—C bond with ring A results also in its deeper penetration within the accessory secondary pocket. In each case, the distance between the sulfonyl S atom and the side chain of Val523 is increased by over 0.1 Å when compared to the respective model compounds, which further to the slight orientation change of ring A, results in closer H-bonds of the sulfonyl oxygens with the NH₂ of Arg513 and His90 by 0.2 and 0.3 Å in average, respectively. Such increases in H-bonding capacity of the sulfonyl oxygens in the secondary binding pocket, along with the slight increase in distance of the C cycle substituent from Arg120 in the primary pocket are sufficient to explain the predicted increases in $pIC_{50}$ by one log unit (see Table 2) [14, 43, 45].

Within the COX-1 binding site (FIGS. (6) and (7)), the minimized structure geometry of the same sila-substituted compounds differ more significantly from those of their respective model compounds, which explains their divergent behaviors in predicted inhibitory activity toward the enzyme. In the case of 1c (FIG. (6)), the rotational angle of cycle C imparted by the sila-substitution removes the CF₃ substituent from the hydroxyl group of Ser530 by 1.34 Å, which consequently removes ring B from Tyr385 by approximately the same distance and brings the sulfonyl substituent of ring A closer to His513. The C cycle rotation brings also the CF₃ substituent in better contact with one NH₂ of Arg120 by 1.07 Å. This explains the decrease in predicted $pIC_{50}$ of 1c for COX-1 by close to two log units, when compared to 1 (Table 2) [17, 38, 44]. In contrast, the rotational angle of cycle C imparted by the sila-substitution in 6b (FIG. (7)), brings the Cl substituent closer to Ser530 by 2.57 Å when compared to the model compound 6, which not only results in a deeper penetration of ring B in the hydrophobic pocket made by Tyr385-Trp387 by 0.53 Å, but removes also the sulfonyl group from His90 and Arg513 by 0.25 Å in average and removes the C cycle Cl substituent from Arg120 by 0.71 Å. This difference in orientation within the COX-1 binding site explains the increased predicted $pIC_{50}$ of 6b by 1.5 log unit when compared to the parent compound 6 (Table 2) [17, 38, 44]. Thus, despite a similar geometry of insertion between the respective pairs 1-1c and 6-6b within the COX-2 binding site, with improvements in critical contacts explaining the increase in predicted $pIC_{50}$ for the sila-substituted compounds, the different orientations between the same pairs within the COX-1 binding site and the resulting opposite differences in predicted inhibitory activity, explain the increase in predicted selectivity index for COX-2 of the former pair of compounds and the relative selectivity index stability of the latter.

The preliminary results obtained during the present study by a comparative computational docking evaluation of sila-substituted COX-2 inhibitors demonstrate that suitable sila-substitutions modulate the selectivity of NSAIDs for COX isozymes and generate highly selective COX-2 inhibitors.

III. Methods

The ligand molecules were constructed in pdb format using the DS viewerPro program from Accelrys Inc and were energy minimized with a convergence of 0.01 Kcal/mol using the Alchemy 2000 program from Tripos Inc. The SciLogP module of the Alchemy 2000 program was then used to calculate the molecular weight (M.W.), volume, surface and the octanol/water partition coefficient (LogP) of each compound. The respective X-ray crystal structures of murine COX-2 complexed with Sc-558 (entry code 6COX) [8] and murine COX-1 complexed with flurbiprofen (entry code 1CQE) [47] were obtained from the pdb. The structures were stripped of ligand and water molecules. The docking experiments were performed by spherical polar Fourier correlations using the Hex 4.2 program available at the website produced by placing "http://www." before "biochem.abdn.ac.uk" [48]. The enzyme structure stripped of inhibitor was used as the receptor and hydrogens were added. The original structure containing the inhibitor was used as complex template. The ligand was fit on the template and docking within the receptor was performed with full rotation allowed by 1280 steps of 5 degree (deg.) each, and a twist angle search of +/−7.5 deg. by steps of 1.4 deg. from the starting orientation, within a distance range of 5 Å by steps of 0.1 Å. Molecular mechanics energy minimization was applied and used to calculate the total binding energy (Ebind) for each docking solution, of which that with the lowest Ebind was selected. The distances between atoms of the energy minimized docked ligand structures and atoms of residues within the respective COX binding sites were evaluated using the DS Viewer Pro program. The cross-validated squared coefficient of correlation $q^2$ within the model compounds group, between experimental (exp.) and predicted (pred.) selectivity index (SI) for COX-2, was calculated using the following formula:

$$q^2 = 1 - \frac{\sum (SI_{exp.} - SI_{pred.})^2}{\sum (SI_{exp.} - SI_{mean})^2}$$

with the standard error of prediction ($SE_{pred.}$) calculated according to the formula:

$$SE_{pred.} = \sqrt{\frac{\sum (SI_{ped.} - SI_{exp.})^2}{n-2}}$$

where n is the number of observations.

IV. Citations

[1] Dubois, R. N.; Abramson, S. B.; Crofford, L.; Gupta, R. A.; Simon, L. S.; van de Pute, L. B.; Lipsky, P. E. FASEB J., 1998, 12, 1063.

[2] Vane, J. R. Nature New Biol., 1971, 231, 232.

[3] Smith, W. L.; Garavito, R. M.; DeWitt, D. L. J. Biol. Chem., 1996, 271, 33157.

[4] Englebienne, P. Drug Design Rev.—Online, 2004, 1, 53.

[5] Marnett, L. J.; Kagutkar, A. S. Curr. Opin. Chem. Biol., 1998, 2, 482.

[6] Gately, S.; Li, W. W. Semin. Oncol., 2004, 31 (Suppl. 7), 2.

[7] Fabiola, G. F.; Pattabhi, V.; Nagarajan, K. Bioorg. Med. Chem., 1998, 6, 2337.

[8] Kurumbail, R. G.; Stevens, A. M.; Gierse, J. K.; McDonald, J. J.; Stegeman, R. A.; Pak, J. Y.; Gildehaus, D.; Miyashiro, J. M.; Penning, T. D.; Seibert, K.; Isakson, P. C.; Stallings, W. C. Nature, 1996, 384, 644.

[9] Prasit, P.; Riendeau,D. Annu. Rep. Med. Chem., 1997, 32, 211.

[10] Talley, J. J.; Brown, D. L.; Carter, J. S.; Graneto, M. J.; Koboldt, C. M.; Masferrer, J. L.; Perkins, W. E.; Rogers, R. S.; Shaffer, A. F.; Zhang, Y. Y.; Zweifel, B. S.; Seibert, K. J. Med. Chem., 2000, 43, 775.

[11] Prasit, P.; Wang, Z.; Brideau, C.; Chan, C. C.; Charleson, S.; Cromlish, W.; Ethier, D.; Evans, J. F.; Ford-Hutchinson, A. W.; Gauthier, J. Y.; Gordon, R.; Guay, J.; Gresser, M.; Kargman, S.; Kennedy, B.; Leblanc, Y.; Leger, S.; Mancini, J.; O'Neill, G.P.; Ouellet, M.; Percival, M. D.; Perrier, H.; Riendeau, D.; Rodger, I.; Tagari, P.; Therien, M.; Vickers, P.; Wong, E.; Xu, L. J.; Young, R. N.; Zamboni, R. Bioorg. Med. Chem. Lett., 1999, 9, 1773.

[12] Friesen, R. W.; Brideau, C.; Chan, C. C.; Charleson, S.; Deschenes, D.; Dube, D.; Ethier, D.; Fortin, R.; Gauthier, J. Y.; Girard, Y.; Gordon, R.; Greig, G. M.; Riendeau, D.; Savoie, C.; Wang, Z.; Wong, E.; Visco, D.; Xu, L. J.; Young, R. N. Bioorg. Med. Chem. Lett., 1998, 8, 2777.

[13] Habeeb, A. G.; Rao, P. N. P.; Knaus, E. E. J. Med. Chem., 2001, 44, 3039.

[14] Uddin, M. J.; Rao, P. N. P.; Knaus, E. E. Bioorg. Med. Chem. Lett., 2003, 11, 5273.

[15] Singh, S. K.; Vobbalareddy, S.; Shivaramakrishna, S.; Krishnamraju, A.; Rajjak, S. A.; Casturi, S. R.; Akhila, V.; Rao, Y. K. Bioorg. Med. Chem. Lett., 2004, 14,1683.

[16] Showell, G. A.; Mills, J. S. Drug Discovery Today, 2003, 8, 551.

[17] Filizola, M.; Perez, J. J.; Palomer, A.; Mauleon, D. J. Mol. Graphics Model., 1997, 15, 290.

[18] Campbell, S. J.; Gold, N. D.; Jackson, R. M.; Westhead, D. R. Curr. Opin. Struct. Biol., 2003, 13, 389.

[19] Alvarez, J. C. Curr. Opin. Chem. Biol., 2004, 8, 1.

[20] Li, J. J.; Anderson, G. D.; Burton, E. G.; Cogburn, J. N.; Collins, J. T.; Garland, D. J.; Gregory, S. A.; Huang, H. C.; lsakson, P. C.; Koboldt, C. M.; Logusch, E. W.; Norton, M. B.; Perkins, W. E.; Reinhard, E. J.; Seibert, K.; Veenhuizen, A. W.; Zhang, Y.; Reitz, D. B. J. Med. Chem., 1995, 38, 4570.

[21] Shin, S. S.; Byun, Y.; Lim, K. M.; Choi, J. K.; Lee, K. W.; Moh, J. H.; Kim, J. K.; Jeong, Y. S.; Kim, J.Y.; Choi, Y. H.; Koh, H. J.; Park, Y. H.; Oh, Y. I.; Noh, M. S.; Chung, S. J. Med. Chem., 2004, 47, 792.

[22] Rao, P. N. P.; Amini, M.; Li, H.; Habeeb, A. G.; Knaus, E. E. J. Med. Chem., 2003, 46, 4872.

[23] Khanna, I.K.; Yu, Y.; Huff, R. M.; Weier, R. M.; Xu, X.; Koszyk, F. J.; Collins, P. W.; Cogburn, J. N., Isakson, P. C.; Koboldt, C. M.; Masferrer, J. L.; Perkins, W. E.; Seibert, K.; Veenhuizen, A. W.; Yuan, J.; Yang, D. C.; Zhang, Y. Y. J. Med. Chem., 2000, 43, 3168.

[24] Ezbiansky, K.; Djurovich, P. I.; LaForest, M.; Sinning, D. J.; Zayes, R.; Berry, D. H. Organometallics, 1998, 17, 1455.

[25] Kakiuchi, F.; Matsumoto, M.; Tsuchiya, K.; Igi, K.; Hayamizu, T.; Chatani, N.; Murai, S. J. Organometal. Chem., 2003, 686, 134.

[26] Ishikawa, M.; Okazaki, S.; Naka, A.; Sakamoto, H. Organometallics, 1992, 11, 4135.

[27] Yamaguchi, S.; Tamao, K. J. Chem. Soc., Dalton Trans., 1998, 3693.

[28] Tang, B. Z.; Zhan, X.; Yu, G.; Lee, P. P. S.; Liu, Y.; Zhu, D. J. Mater. Chem., 2001, 11, 2974.

[29] Cai, Y.; Roberts, B. P. J. Chem. Soc., Perkin Trans. 1, 1998, 467.

[30] Losehand, U.; Mitzel, N. W. J. Chem. Soc., Dalton Trans., 2000, 1049.

[31] Bowman, W. R.; Cloonan, M. O.; Krintel, S. L. J. Chem. Soc., Perkin Trans. 1, 2001, 2885.

[32] Sakai, N.; Fukushima, T.; Okada, O.; Ohashi, S.; Minakata, S.; Komatsu, M. J. Organometal. Chem., 2003, 686, 368.

[33] Heinonen, P.; Sipila, H.; Neuvonen, K.; Lönnberg, H.; Cockcroft, V. B.; Wurster, S.; Virtanen, R.; Savola, M. K. T.; Salonen, J. S.; Savola, J. M. Eur. J. Med. Chem., 1996, 31, 725.

[34] Felder, C. C.; Bymaster, F. P.; Ward, J.; DeLapp, N. J. Med. Chem., 2000, 43, 4333.

[35] Tacke, R.; Handmann, V. I.; Kreutzmann, K.; Keim, C.; Mutschler, E.; Lambrecht, G. Organometallics, 2002, 21, 3727.

[36] Tacke, R.; Handmann, V. I.; Bertermann, R.; Burschka, C.; Penka, M.; Seyfried, C. Organometallics, 2003, 22, 916.

[37] Heinrich, T.; Burschka, C.; Warneck, J.; Tacke, R. Organometallics, 2004, 23, 361.

[38] Liu, H.; Huang, X.; Shen, J.; Luo, X.; Li, M.; Xiong, B.; Chen, G.; Shen, J.; Yang, Y.; Jiang, H.; Chen, K. J. Med. Chem., 2002, 45, 4816.

[39] Desiraju, G. R.; Gopalakrishnan, B.; Jetti, R. K. R.; Nagaraju, A.; Raveendra, D.; Sarma, J. A. R. P.; Sobhia, M. E.; Thilagavathi, R. J. Med. Chem., 2002, 45, 4847.

[40] Rao, P. N.; Amini, M.; Li, H.; Habeeb, A. G.; Knaus, E. E. Bioorg. Med. Chem. Lett., 2003, 13, 2205.

[41] Kim, H. J.; Chae, C. H.; Yi, K. Y.; Park, K. L.; Yoo, S. Bioorg. Med. Chem., 2004, 12, 1629.

[42] Fabiola, G. F.; Pattabhi, V.; Nagarajan, K. Bioorg. Med. Chem., 1998, 6, 2337.

[43] Pal, M.; Madan, M.; Padakanti, S.; Pattabiraman, V. R.; Kalleda, S.; Vanguri, A.; Mullangi, R.; Mamidi, N. V. S. R.; Casturi, S. R.; Malde, A.; Gopalakrishnan, B.; Yeleswarapu, K. R. J. Med. Chem., 2003, 46, 3975.

[44] Soliva, R.; Almansa, C.; Kalko, S. G., Luque, F. J.; Orozco, M. J. Med. Chem., 2003, 46, 1372.

[45] Hood, W. F.; Gierse, J. K.; Isakson, P. C.; Kiefer, J. R.; Kurumbail, R. G.; Seibert, K.; Monahan, J. B. Mol. Pharmacol., 2003, 63, 870.

[46] Palomer, A.; Cabré, F.; Pascual, J.; Campos, J.; Trujillo, M. A.; Entrena, A.; Gallo, M. A.; Garcia, L.; Mauleon, D.; Espinosa, A. J. Med. Chem., 2002, 45, 1402.

[47] Picot, D.; Loll, P. J.; Garavito, R. M. Nature, 1994, 367, 243.

[48] Ritchie, D. W.; Kemp, G. J. L. J. Comp. Chem., 1999, 20, 383.

It is evident from the above results and discussion that the subject invention provides an important new class of selective COX-2 inhibitory compounds that find use in a variety of different applications. Advantages of embodiments of compounds of the invention include one or more of: altered in vitro potency; altered rate of metabolism, improved potency, improved in vivo half-life, improved tissue distribution, etc., as compared to analogous compounds that lack at least one silicon atom. As such, the subject invention provides a significant contribution to the art.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention.

What is claimed is:

1. A silicon-containing compound having selective COX-2 inhibitor activity, wherein said compound is selected from the group consisting of: 4-[5-(4-Bromophenyl)-3-trimethylsilanyl-pyrazol-1-yl]-benzenesulfonamide, 2-(4-Bromophenyl)-2-(4-methanesulfonylphenyl)-5-trifluoromethyl-2H-[1,2]azasilole, 4-[3-(4-Bromophenyl)-5-trifluoromethyl-3H-[1,2,3]diazasilol-3-yl]-benzenesulfonamide, 4-[5-(4-Bromophenyl)-3,3-dimethyl-2,3-dihydro-[1,2,3]diazasilol-1-yl]-benzenesulfonamide, 4-(5-p-Tolyl-3-trimethylsilanyl-pyrazol-1-yl)-benzenesulfonamide, 4-(2-p-Tolyl-5-trifluoromethyl-2H-[1,2]azasilol-2-yl)-benzenesulfonamide, 4-(3-p-Tolyl-5-trifluoromethyl-3H-[1,2,3]diazasilol-3-yl)-benzenesulfonamide, 4-(3,3-Dimethyl-5-p-tolyl-2,3-dihydro-[1,2,3]diazasilol-1-yl)-benzenesulfonamide, 4-(4-Fluorophenyl)-5-(4-methanesulfonylphenyl)-1,1-dimethyl-2,3-dihydro-1H-silole, 3-(4-Fluorophenyl)-4-(4-methanesulfonylphenyl)-1,1-dimethyl-2,5-dihydro-1H-silole, 5-(4-Fluorophenyl)-4-(4-methanesulfonylphenyl)-1,1-dimethyl-2,3-dihydro-1H-silole, 1-(4-Fluorophenyl)-1-(4-methanesulfonylphenyl)-silolane, 1-(4-Fluorophenyl)-1-(4-methanesulfonylphenyl)-2,3-dihydro-1H-silole, 4-(3-Phenyl-5-trimethylsilanyl-isoxazol-4-yl)-benzenesulfonamide, 4-(5-Methyl-4-phenyl-4,5-dihydro-[1,2,4]oxazasilol-4-yl)-benzenesulfonamide, 4-(5-Methyl-3-phenyl-2,3-dihydro-[1,2,3]oxazasilol-3-yl)-benzenesulfonamide, 4-(5,5-Dimethyl-3-phenyl-4,5-dihydro-[1,2,5]oxazasilol-4-yl)-benzenesulfonamide, 3-(4-Methanesulfonylphenyl)-2,2-dimethyl-4-phenyl-2H-[1,2]oxasilol-5-one, 3-(4-Methanesulfonylphenyl)-3-phenyl-[1,3]oxasilolan-5-one, 3-(4-Methanesulfonylphenyl)-3-phenyl-3H-[1,3]oxasilol-2-one, 5-Chloro-3-(4-methanesulfonylphenyl)-3-(6-methylpyridin-3-yl)-2,3-dihydro-[1,3]azasiline, 5-Chloro-2-(4-methanesulfonylphenyl)-2-(6-methylpyridin-3-yl)-2,3-dihydro-[1,2]azasiline, 6-Ethoxy-4-(4-fluorophenyl)-3-(4-methanesulfonylphenyl)-3,4-dihydro-[1,3]oxasilin-2-one, 6-Ethoxy-4-(4-fluorophenyl)-4-(4-methanesulfonylphenyl)-3,4-dihydro-[1,4]oxasilin-2-one, 6-Ethylsulfanyl-3-(4-methanesulfonylphenyl)-3-phenyl-3,4-dihydro-[1,3]oxasilin-2-one, 6-Ethylsulfanyl-4-(4-methanesulfonylphenyl)-4-phenyl-3,4-dihydro-[1,4]oxasilin-2-one, 4-(4-Butylphenyl)-5-(4-methanesulfonylphenyl)-2,2-dimethyl-[1,2]oxasilol-3-one, 2-(4-Butylphenyl)-2-(4-methanesulfonylphenyl)-5,5-dimethyl-[1,2]oxasilolan-4-one, 5-(4-Butylphenyl)-5-(4-methanesulfonylphenyl)-2,2-dimethyl-[1,2,5]oxadisilolan-3-one, 3-[1-(4-Methanesulfonylphenyl)-4-trimethylsilanyl-1H-imidazol-2-yl]-pyridine, 3-[2-(4-Methanesulfonylphenyl)-4-trifluoromethyl-2H-[1,3,2]diazasilol-2-yl]-pyridine, 1-(4-Methanesulfonylphenyl)-2-phenyl-4-trimethylsilanyl-1H-imidazole, 1-(4-Methanesulfonylphenyl)-2-phenyl-4-trifluoromethyl-2H-[1,3,2]diazasilole.

2. A method of relieving an inflammatory condition in a subject by inhibiting COX-2 enzymes, said method comprising administering to said subject an effective amount of a silicon containing compound having COX-2 inhibitory activity, wherein said compound is selected from the group consisting of: 4-[5-(4-Bromophenyl)-3-trimethylsilanyl-pyrazol-1-yl]-benzenesulfonamide, 2-(4-Bromophenyl)-2-(4-methanesulfonylphenyl)-5-trifluoromethyl-2H-[1,2]azasilole, 4-[3-(4-Bromophenyl)-5-trifluoromethyl-3H-[1,2,3]diazasilol-3-yl]-benzenesulfonamide, 4-[5-(4-Bromophenyl)-3,3-dimethyl-2,3-dihydro-[1,2,3]diazasilol-1-yl]-benzenesulfonamide, 4-(5-p-Tolyl-3-trimethylsilanyl-pyrazol-1-yl)-benzenesulfonamide, 4-(2-p-Tolyl-5-trifluoromethyl-2H-[1,2]azasilol-2-yl)-benzenesulfonamide, 4-(3-p-Tolyl-5-trifluoromethyl-3H-[1,2,3]diazasilol-3-yl)-benzenesulfonamide, 4-(3,3-Dimethyl-5-p-tolyl-2,3-dihydro-[1,2,3]diazasilol-1-yl)-benzenesulfonamide, 4-(4-Fluorophenyl)-Lole-(4-methanesulfonylphenyl)-1,1-dimethyl-2,3-dihydro-1H-silole, 3-(4-Fluorophenyl)-4-(4-methanesulfonylphenyl)-1,1-dimethyl-2,5-dihydro-1H-silole, 5-(4-Fluorophenyl)-4-(4-methanesulfonylphenyl)-1,1-dimethyl-2,3-dihydro-1H-silole, 1-(4-Fluorophenyl)-1-(4-methanesulfonylphenyl)-silolane, 1-(4-Fluorophenyl)-1-(4-methanesulfonylphenyl)-2,3-dihydro-1H-silole, 4-(3-Phenyl-5-trimethylsilanyl-isoxazol-4-yl)-benzenesulfonamide, 4-(5-Methyl-4-phenyl-4,5-dihydro-[1,2,4]oxazasilol-4-yl)-benzenesulfonamide, 4-(5-Methyl-3-phenyl-2,3-dihydro-[1,2,3]oxazasilol-3-yl)-benzenesulfonamide, 4-(5,5-Dimethyl-3-phenyl-4,5-dihydro-[1,2,5]oxazasilol-4-yl)-benzenesulfonamide, 3-(4-Methanesulfonylphenyl)-2,2-dimethyl-4-phenyl-2H-[1,2]oxasilol-5-one, 3-(4-Methanesulfonylphenyl)-3-phenyl-[1,3]oxasilolan-5-one, 3-(4-Methanesulfonylphenyl)-3-phenyl-3H-[1,3]oxasilol-2-one, 5-Chloro-3-(4-methanesulfonylphenyl)-3-(6-methylpyridin-3-yl)-2,3-dihydro-[1,3]azasiline, 5-Chloro-2-(4-methanesulfonylphenyl)-2-(6-methylpyridin-3-yl)-2,3-dihydro-[1,2]azasiline, 6-Ethoxy-4-(4-fluorophenyl)-3-(4-methanesulfonylphenyl)-3,4-dihydro-[1,3]oxasilin-2-one, 6-Ethoxy-4-(4-fluorophenyl)-4-(4-methanesulfonylphenyl)-3,4-dihydro-[1,4]oxasilin-2-one, 6-Ethylsulfanyl-3-(4-methanesulfonylphenyl)-3-phenyl-3,4-dihydro-[1,3]oxasilin-2-one, 6-Ethylsulfanyl-4-(4-methanesulfonylphenyl)-4-phenyl-3,4-dihydro-[1,4]oxasilin-2-one, 4-(4-Butylphenyl)-5-(4-methanesulfonylphenyl)-2,2-dimethyl-[1,2]oxasilol-3-one, 2-(4-Butylphenyl)-2-(4-methanesulfonylphenyl)-5,5-dimethyl-[1,2]oxasilolan-4-one, 5-(4-Butylphenyl)-5-(4-methanesulfonylphenyl)-2,2-dimethyl-[1,2,5]oxadisilolan-3-one, 3-[1-(4-Methanesulfonylphenyl)-4-trimethylsilanyl-1H-imidazol-2-yl]-pyridine, 3-[2-(4-Methanesulfonylphenyl)-4-trifluoromethyl-2H-[1,3,2]diazasilol-2-yl]-pyridine, 1-(4-Methanesulfonylphenyl)-2-phenyl-4-trimethylsilanyl-1H-imidazole, 1-(4-Methanesulfonylphenyl)-2-phenyl-4-trifluoromethyl-2H-[1,3,2]diazasilole.

3. A composition comprising a silicon-containing compound having COX-2 inhibitory activity in a pharmaceutically acceptable vehicle, wherein said compound is selected from the group consisting of: 4-[5-(4-Bromophenyl)-3-trimethylsilanyl-pyrazol-1-yl]-benzenesulfonamide, 2-(4-Bromophenyl)-2-(4-methanesulfonylphenyl)-5-trifluoromethyl-2H-[1,2]azasilole, 4-[3-(4-Bromophenyl)-5-trifluoromethyl-3H-[1,2,3]diazasilol-3-yl]-benzenesulfonamide, 4-[5-(4-Bromophenyl)-3,3-dimethyl-2,3-dihydro-[1,2,3]diazasilol-1-yl]-benzenesulfonamide, 4-(5-p-Tolyl-3-trimethylsilanyl-pyrazol-1-yl)-benzenesulfonamide, 4-(2-p-Tolyl-5-trifluoromethyl-2H-[1,2]azasilol-2-yl)-benzenesulfonamide, 4-(3-p-Tolyl-5-trifluoromethyl-3H-[1,2,3]diazasilol-3-yl)-benzenesulfonamide, 4-(3,3-Dimethyl-5-p-tolyl-2,3-dihydro-[1,2,3]diazasilol-1-yl)-benzenesulfonamide, 4-(4-Fluorophenyl)-5-(4-methanesulfonylphenyl)-1,1-dimethyl-2,3-dihydro-1H-silole, 3-(4-Fluorophenyl)-4-(4-methanesulfonylphenyl)-1,1-dimethyl-2,5-dihydro-1H-silole, 5-(4-Fluorophenyl)-4-(4-methanesulfonylphenyl)-1,1-dimethyl-2,3-dihydro-1H-silole, 1-(4-Fluorophenyl)-1-(4-methanesulfonylphenyl)-silolane, 1-(4-Fluorophenyl)-1-(4-methanesulfonylphenyl)-2,3-dihydro-1H-silole, 4-(3-Phenyl-5-trimethylsilanyl-isoxazol-4-yl)-benzenesulfonamide, 4-(5-Methyl-4-phenyl-4,5-dihydro-[1,2,4]oxazasilol-4-yl)-benzenesulfonamide, 4-(5-Methyl-3-phenyl-2,3-dihydro-[1,2,3]oxazasilol-3-yl)-benzenesulfonamide, 4-(5,5-Dimethyl-3-phenyl-4,5-dihydro-[1,2,5]oxazasilol-4-yl)-benzenesulfonamide, 3-(4-Methanesulfonylphenyl)-2,2-dimethyl-4-phenyl-2H-[1,2]

oxasilol-5-one, 3-(4-Methanesulfonylphenyl)-3-phenyl-[1,3]oxasilolan-5-one, 3-(4-Methanesulfonylphenyl)-3-phenyl-3H-[1,3]oxasilol-2-one, 5-Chloro-3-(4-methanesulfonylphenyl)-3-(6-methylpyridin-3-yl)-2,3-dihydro-[1,3]azasiline, 5-Chloro-2-(4-methanesulfonylphenyl)-2-(6-methylpyridin-3-yl)-2,3-dihydro-[1,2]azasiline, 6-Ethoxy-4-(4-fluorophenyl)-3-(4-methanesulfonylphenyl)-3,4-dihydro-[1,3]oxasilin-2-one, 6-Ethoxy-4-(4-fluorophenyl)-4-(4-methanesulfonylphenyl)-3,4-dihydro-[1,4]oxasilin-2-one, 6-Ethylsulfanyl-3-(4-methanesulfonylphenyl)-3-phenyl-3,4-dihydro-[1,3]oxasilin-2-one, 6-Ethylsulfanyl-4-(4-methanesulfonylphenyl)-4-phenyl-3,4-dihydro-[1,4]oxasilin-2-one, 4-(4-Butylphenyl)-5-(4-methanesulfonylphenyl)-2,2-dimethyl-[1,2]oxasilol-3-one, 2-(4-Butylphenyl)-2-(4-methanesulfonylphenyl)-5,5-dimethyl-[1,2]oxasilolan-4-one, 5-(4-Butylphenyl)-5-(4-methanesulfonylphenyl)-2,2-dimethyl-[1,2,5]oxadisilolan-3-one, 3-[1-(4-Methanesulfonylphenyl)-4-trimethylsilanyl-1H-imidazol-2-yl]-pyridine, 3-[2-(4-Methanesulfonylphenyl)-4-trifluoromethyl-2H-[1,3,2]diazasilol-2-yl]-pyridine, 1-(4-Methanesulfonylphenyl)-2-phenyl-4-trimethylsilanyl-1H-imidazole, 1-(4-Methanesulfonylphenyl)-2-phenyl-4-trifluoromethyl-2H-[1,3,2]diazasilole.

4. A kit comprising:
a silicon-containing compound having COX-2 inhibitory activity, wherein said compound is selected from the group consisting of: 4-[5-(4-Bromophenyl)-3-trimethylsilanyl-pyrazol-1-yl]-benzenesulfonamide, 2-(4-Bromophenyl)-2-(4-methanesulfonylphenyl)-5-trifluoromethyl-2H-[1,2]azasilole, 4-[3-(4-Bromophenyl)-5-trifluoromethyl-3H-[1,2,3]diazasilol-3-yl]-benzenesulfonamide, 4-[5-(4-Bromophenyl)-3,3-dimethyl-2,3-dihydro-[1,2,3]diazasilol-1-yl]-benzenesulfonamide, 4-(5-p-Tolyl-3-trimethylsilanyl-pyrazol-1-yl)-benzenesulfonamide, 4-(2-p-Tolyl-5-trifluoromethyl-2H-[1,2]azasilol-2-yl)-benzenesulfonamide, 4-(3-p-Tolyl-5-trifluoromethyl-3H-[1,2,3]diazasilol-3-yl)-benzenesulfonamide, 4-(3,3-Dimethyl-5-p-tolyl-2,3-dihydro-[1,2,3]diazasilol-1-yl)-benzenesulfonamide, 4-(4-Fluorophenyl)-5-(4-methanesulfonylphenyl)-1,1-dimethyl-2,3-dihydro-1H-silole, 3-(4-Fluorophenyl)-4-(4-methanesulfonylphenyl)-1,1-dimethyl-2,5-dihydro-1H-silole, 5-(4-Fluorophenyl)-4-(4-methanesulfonylphenyl)-1,1-dimethyl-2,3-dihydro-1H-silole, 1-(4-Fluorophenyl)-1-(4-methanesulfonylphenyl)-silolane, 1-(4-Fluorophenyl)-1-(4-methanesulfonylphenyl)-2,3-dihydro-1H-silole, 4-(3-Phenyl-5-trimethylsilanyl-isoxazol-4-yl)-benzenesulfonamide, 4-(5-Methyl-4-phenyl-4,5-dihydro-[1,2,4]oxazasilol-4-yl)-benzenesulfonamide, 4-(5-Methyl-3-phenyl-2,3-dihydro-[1,2,3]oxazasilol-3-yl)-benzenesulfonamide, 4-(5,5-Dimethyl-3-phenyl-4,5-dihydro-[1,2,5]oxazasilol-4-yl)-benzenesulfonamide, 3-(4-Methanesulfonylphenyl)-2,2-dimethyl-4-phenyl-2H-[1,2]oxasilol-5-one, 3-(4-Methanesulfonylphenyl)-3-phenyl-[1,3]oxasilolan-5-one, 3-(4-Methanesulfonylphenyl)-3-phenyl-3H-[1,3]oxasilol-2-one, 5-Chloro-3-(4-methanesulfonylphenyl)-3-(6-methylpyridin-3-yl)-2,3-dihydro-[1,3]azasiline, 5-Chloro-2-(4-methanesulfonylphenyl)-2-(6-methylpyridin-3-yl)-2,3-dihydro-[1,2]azasiline, 6-Ethoxy-4-(4-fluorophenyl)-3-(4-methanesulfonylphenyl)-3,4-dihydro-[1,3]oxasilin-2-one, 6-Ethoxy-4-(4-fluorophenyl)-4-(4-methanesulfonylphenyl)-3,4-dihydro-[1,4]oxasilin-2-one, 6-Ethylsulfanyl-3-(4-methanesulfonylphenyl)-3-phenyl-3,4-dihydro-[1,3]oxasilin-2-one, 6-Ethylsulfanyl-4-(4-methanesulfonylphenyl)-4-phenyl-3,4-dihydro-[1,4]oxasilin-2-one 4-(4-Butylphenyl)-5-(4-methanesulfonylphenyl)-2,2-dimethyl-[1,2]oxasilol-3-one, 2-(4-Butylphenyl)-2-(4-methanesulfonylphenyl)-5,5-dimethyl-[1,2]oxasilolan-4-one, 5-(4-Butylphenyl)-5-(4-methanesulfonylphenyl)-2,2-dimethyl-[1,2,5]oxadisilolan-3-one, 3-[1-(4-Methanesulfonylphenyl)-4-trimethylsilanyl-1H-imidazol-2-yl]-pyridine, 3-[2-(4-Methanesulfonylphenyl)-4-trifluoromethyl-2H-[1,3,2]diazasilol-2-yl]-pyridine, 1-(4-Methanesulfonylphenyl)-2-phenyl-4-trimethylsilanyl-1H-imidazole, 1-(4-Methanesulfonylphenyl)-2-phenyl-4-trifluoromethyl-2H-[1,3,2]diazasilole; and
instructions of using said compound.

* * * * *